United States Patent
Zhang et al.

(10) Patent No.: US 12,089,910 B2
(45) Date of Patent: Sep. 17, 2024

(54) MOBILE-ELECTROMAGNETIC COIL-BASED MAGNETIC ACTUATION SYSTEMS

(71) Applicant: The Chinese University of Hong Kong, Hong Kong (CN)

(72) Inventors: Li Zhang, Hong Kong (CN); Xingzhou Du, Hong Kong (CN); Kai Fung Chan, Hong Kong (CN); Lidong Yang, Hong Kong (CN); Moqiu Zhang, Hong Kong (CN)

(73) Assignee: The Chinese University of Hong Kong, Hong Kong (CN)

( * ) Notice: Subject to any disclaimer, the term of this patent is extended or adjusted under 35 U.S.C. 154(b) by 533 days.

(21) Appl. No.: 16/885,718

(22) Filed: May 28, 2020

(65) Prior Publication Data
US 2021/0369373 A1    Dec. 2, 2021

(51) Int. Cl.
*B25J 13/08*    (2006.01)
*A61B 17/00*    (2006.01)
*A61B 34/00*    (2016.01)

(52) U.S. Cl.
CPC ........ *A61B 34/73* (2016.02); *A61B 17/00234* (2013.01); *B25J 13/088* (2013.01)

(58) Field of Classification Search
CPC ... A61B 34/73; A61B 17/00234; A61B 34/30; A61B 90/361; A61B 2017/00725;
(Continued)

(56) References Cited

U.S. PATENT DOCUMENTS 4,672,951 A * 6/1987 Welch ............... A61N 1/40
                                                600/14
5,357,779 A * 10/1994 Hahn ............... B21D 22/28
                                                72/347
(Continued)

FOREIGN PATENT DOCUMENTS

CA    2605912 A1 * 11/2006 ......... A61B 1/00158
CN    100438826 C * 12/2008 ............ A61B 17/22
(Continued)

OTHER PUBLICATIONS

"RoboMag: A Magnetic Actuation System Based on Mobile Electromagnetic Coils With Tunable Working Space;" Du et al., 2020 5th International Conference on Advanced Robotics and Mechatronics (ICARM) (pp. 125-131); Dec. 1, 2020. (Year: 2020).*
(Continued)

*Primary Examiner* — Khoi H Tran
*Assistant Examiner* — Jorge O Peche
(74) *Attorney, Agent, or Firm* — Kilpatrick Townsend & Stockton LLP

(57) ABSTRACT

Magnetic field has been considered as a safe and promising method for remote control of medical robots in body. Systems that implement electromagnetic coils can provide wide control bandwidth and on-off capability. However, scaling-up the working space of such systems for clinical use and increasing energy efficiency to reduce heat generation have always been a challenging task. The design, modeling and control methods for a magnetic actuation system with multiple mobile electromagnetic coils with decoupled movements are introduced. The high flexibility of such configuration and the proposed real-time control strategy enables the system to enlarge the working space by tracking the locomotion of the robot, deal with the irregularly shaped obstructions inside the working area, work with medical imaging systems for localization of the medical (Continued)

robots, generate various kind of magnetic field for actuation and conduct real-time optimization on coils' positions to enhance energy efficiency.

16 Claims, 15 Drawing Sheets

(58) Field of Classification Search
CPC .. A61B 2034/2059; A61B 2017/00411; A61B 2017/00876; A61B 2034/2051; A61B 2034/301; A61B 2034/731; A61B 2034/732; B25J 13/088
See application file for complete search history.

(56) References Cited

U.S. PATENT DOCUMENTS

| | | | |
|---|---|---|---|
| 6,311,082 B1 | 10/2001 | Creighton, IV et al. | |
| 6,958,672 B1* | 10/2005 | Shen | G01R 33/383 |
| | | | 335/298 |
| 7,769,427 B2* | 8/2010 | Shachar | A61B 5/7455 |
| | | | 606/1 |
| 8,058,865 B2* | 11/2011 | May | G01D 5/2046 |
| | | | 324/207.16 |
| 10,004,566 B2 | 6/2018 | Park et al. | |
| 10,165,962 B2* | 1/2019 | Messerly | A61B 46/10 |
| 10,238,418 B2* | 3/2019 | Cox | A61B 8/4254 |
| 11,834,204 B1* | 12/2023 | Gorokhovsky | F03H 1/0043 |
| 2004/0019447 A1* | 1/2004 | Shachar | A61B 5/062 |
| | | | 702/115 |
| 2005/0096589 A1* | 5/2005 | Shachar | A61B 5/064 |
| | | | 604/95.01 |
| 2006/0161059 A1* | 7/2006 | Wilson | A61B 90/39 |
| | | | 600/424 |
| 2007/0016006 A1* | 1/2007 | Shachar | A61B 5/062 |
| | | | 600/407 |
| 2007/0197891 A1* | 8/2007 | Shachar | A61B 34/73 |
| | | | 600/374 |
| 2007/0237283 A1* | 10/2007 | Payne | G21C 19/00 |
| | | | 376/261 |
| 2007/0244388 A1* | 10/2007 | Sato | A61B 1/041 |
| | | | 600/550 |
| 2008/0091193 A1* | 4/2008 | Kauphusman | A61B 18/1492 |
| | | | 606/41 |
| 2008/0249395 A1* | 10/2008 | Shachar | A61B 5/062 |
| | | | 600/409 |
| 2009/0153140 A1* | 6/2009 | Tanaka | G01R 33/34053 |
| | | | 324/318 |
| 2009/0159697 A1* | 6/2009 | Mullen | G06Q 20/385 |
| | | | 235/493 |
| 2009/0253985 A1* | 10/2009 | Shachar | A61B 5/064 |
| | | | 600/424 |
| 2009/0299136 A1* | 12/2009 | Hasegawa | A61B 17/00234 |
| | | | 600/106 |
| 2010/0130854 A1* | 5/2010 | Shachar | A61B 5/06 |
| | | | 600/424 |
| 2010/0305429 A1* | 12/2010 | Shachar | A61B 5/06 |
| | | | 600/424 |
| 2011/0301497 A1* | 12/2011 | Shachar | A61B 1/041 |
| | | | 600/114 |
| 2012/0281330 A1 | 11/2012 | Abbott et al. | |
| 2012/0302820 A1* | 11/2012 | Carmeli | A61B 5/0538 |
| | | | 600/12 |
| 2013/0006100 A1* | 1/2013 | Shachar | A61B 34/76 |
| | | | 600/424 |
| 2013/0075368 A1* | 3/2013 | Marchand | H01H 33/662 |
| | | | 218/140 |
| 2013/0303878 A1* | 11/2013 | Nevo | A61B 34/20 |
| | | | 600/409 |
| 2014/0018792 A1* | 1/2014 | Gang | A61B 18/1492 |
| | | | 606/41 |
| 2014/0163664 A1* | 6/2014 | Goldsmith | A61B 17/0057 |
| | | | 604/93.01 |
| 2014/0276948 A1* | 9/2014 | Zirps | A61B 34/35 |
| | | | 606/130 |
| 2015/0005759 A1* | 1/2015 | Welches | A61B 18/1402 |
| | | | 606/34 |
| 2015/0380140 A1 | 12/2015 | Duan et al. | |
| 2016/0111192 A1* | 4/2016 | Suzara | A61B 5/0036 |
| | | | 335/301 |
| 2016/0270810 A1* | 9/2016 | Vardi | A61B 17/32053 |
| 2017/0011876 A1* | 1/2017 | Natti | H01F 7/0268 |
| 2017/0281086 A1* | 10/2017 | Donaldson | A61B 5/1118 |
| 2017/0333137 A1* | 11/2017 | Roessler | A61B 34/30 |
| 2018/0177516 A1* | 6/2018 | Vardi | A61B 17/320016 |
| 2018/0214221 A1* | 8/2018 | Crawford | B25J 13/08 |
| 2018/0340825 A1* | 11/2018 | Suzara | G01J 3/42 |
| 2019/0104994 A1 | 4/2019 | Valdastri et al. | |
| 2019/0187856 A1* | 6/2019 | Bruwer | G06F 3/046 |
| 2019/0192874 A1* | 6/2019 | Shukla | A61N 2/02 |
| 2019/0209080 A1* | 7/2019 | Gullotti | A61B 17/7076 |
| 2019/0343422 A1* | 11/2019 | Shlomovitz | A61B 5/062 |
| 2020/0170662 A1* | 6/2020 | Vardi | A61B 17/320016 |
| 2020/0383603 A1* | 12/2020 | Izmirli | A61B 5/062 |
| 2021/0059779 A1* | 3/2021 | Zhao | B25J 9/1682 |
| 2021/0369373 A1* | 12/2021 | Zhang | B25J 13/088 |
| 2021/0398724 A1* | 12/2021 | Zhang | H01F 27/24 |
| 2022/0160434 A1* | 5/2022 | Messerly | A61B 5/062 |

FOREIGN PATENT DOCUMENTS

| | | | | | |
|---|---|---|---|---|---|
| CN | 106473804 | A | * | 3/2017 | A61B 1/12 |
| CN | 108186120 | A | * | 6/2018 | A61B 17/00234 |
| CN | 113617756 | B | * | 5/2022 | |
| CN | 114654488 | A | * | 6/2022 | |
| CN | 114654489 | A | * | 6/2022 | |
| DE | 69818526 | T2 | * | 7/2004 | |
| DE | 102006045177 | A1 | * | 4/2008 | A61B 34/70 |
| ES | 2525525 | T3 | * | 12/2014 | A61B 5/042 |
| JP | 2021525566 | A | * | 9/2021 | |
| JP | 2021525584 | A | * | 9/2021 | |
| JP | 7130682 | B2 | * | 9/2022 | A61B 1/00149 |
| KR | 101596294 | B1 | * | 2/2016 | |
| WO | WO-2006128160 | A2 | * | 11/2006 | A61B 1/00158 |
| WO | WO-2015085011 | A1 | * | 6/2015 | A61B 1/041 |
| WO | WO-2018020236 | A1 | * | 2/2018 | A61B 17/1746 |
| WO | WO-2020009723 | A1 | * | 1/2020 | A61B 17/7032 |

OTHER PUBLICATIONS

"Design and Real-Time Optimization for a Magnetic Actuation System With Enhanced Flexibility;" Du et al.; IEEE/ASME Transactions on Mechatronics (vol. 26, Issue: 3, pp. 1524-1535); Jun. 1, 2021. (Year: 2021).*
"The ARMM System: An Optimized Mobile Electromagnetic Coil for Non-Linear Actuation of Flexible Surgical Instruments;" Sikorski et al., IEEE Transactions on Magnetics (vol. 55, Issue: 9, pp. 1-9); Jun. 19, 2019. (Year: 2019).*
"Study on Magnetic Control Systems of Micro-Robots," Shao et al.; Frontiers in Neuroscience, 15, 736730; Aug. 26, 2021. (Year: 2021).*
Kummer, et al., "OctoMag: An Electromagnetic System for 5-DOF Wireless Micromanipulation," IEEE Transactions on Robotics, vol. 26, No. 6, pp. 1006-1017 (Dec. 2010).
Mahoney, et al., "Five-degree-of-freedom manipulation of an untethered magnetic device in fluid using a single permanent magnet with application in stomach capsule endoscopy," The International Journal of Robotics Research, vol. 35(1-3), pp. 129-147 (2016).
Taddese, et al., "Enhanced Real-Time Pose Estimation for Closed-Loop Robotic Manipulation of Magnetically Actuated Capsule Endoscopes," The International Journal of Robotics Research, Reprinted by permission of SAGE Publications, pp. 1-25 (2018).

* cited by examiner

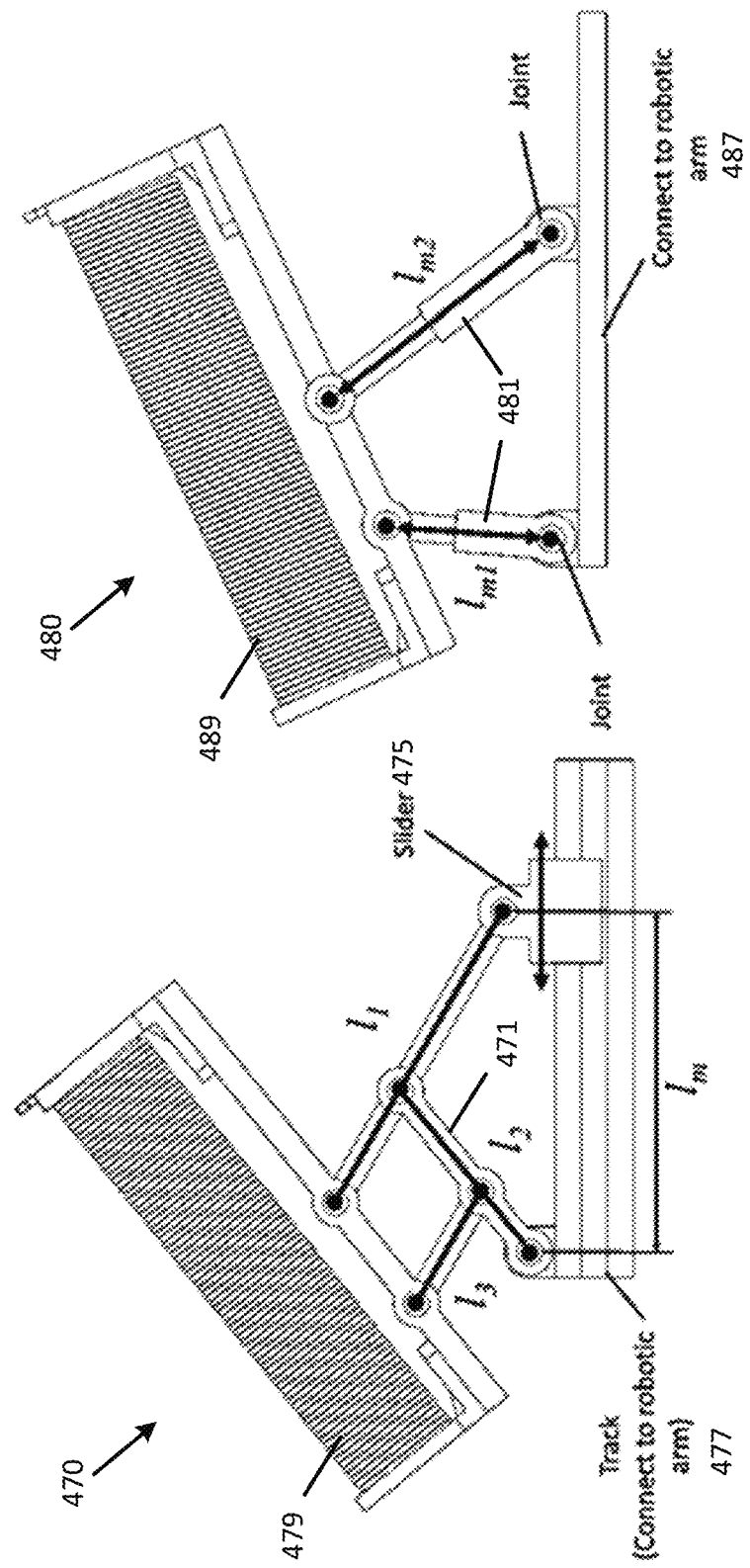

MOBILE-ELECTROMAGNETIC COIL-BASED MAGNETIC ACTUATION SYSTEMS

BACKGROUND

Magnetic field has been considered as a promising strategy to remotely control various tethered or untethered magnetic devices such as medical robots. Such medical robots can range from millimeter-scale magnetic capsule endoscopes and magnetically actuated catheters, all the way down to the micro-scale or nano-scale microrobots and microrobotic swarms. These magnetically actuated medical robots have the properties of tissue penetration capability and high safety for potential applications in minimally invasive surgery and targeted delivery. To control the locomotion or other practical functions of magnetic robotic devices remotely, magnetic actuation systems can be implemented to provide the demanded magnetic field.

BRIEF SUMMARY

Systems and methods for remote navigation and actuation of magnetic medical devices in biomedical applications are described. More particularly, the magnetic actuation system may implement more than one mobile electromagnetic coils that can be individually actuated to demanded positions within a spatial area, and the coils can generate magnetic field to actuate the medical robot remotely. The optimal spatial position and orientation of each coil for magnetic actuation can be calculated through the technique described herein.

A design, modeling, control and optimization method for magnetic actuation systems with decoupled mobile electromagnetic coils is utilized for remote manipulation of medical robots through magnetic field. The system can implement more than one mobile coils that can be individually placed to optimal positions and orientations by mechanical platform, and at the same time avoid collision with the obstructions inside the workspace. The relative positions between the coils can be adjustable or fixed. Demanded magnetic field can be generated by the electromagnetic coils with soft iron core, to actuate or navigate various kind of medical robots to conduct required tasks inside body. The mobility of the coils also endows the system with a large working space by tracking the spatial location of the robot. The maximum working space is determined by the reachable area of the mechanical platform.

Mobile electromagnetic coils with decoupled movements can be implemented. The decoupled mobile electromagnetic coils make the system more flexible to satisfy environmental constrains and reach closer to the magnetic robot inside the body, and therefore be able to generate demanded magnetic field with higher energy efficiency. This allows smaller coils and lower electrical current to be used, so the heat generation can be reduced and the frequency response of each coil can be promoted.

Another advantage of using decoupled mobile electromagnetic coils is its compatibility with intraoperative imaging devices, which can be used for real-time localization of medical robots and feed-back control. The localization devices can be, for example, X-ray imaging devices, ultrasound imaging devices, camera, magnetic field sensors, photoacoustic imaging devices, etc.

More than one electromagnetic coils can be implemented in the magnetic actuation system. By using more than one coil that work simultaneously in a cooperative manner, dynamic alternating magnetic fields can be generated by changing the currents inside each coil, and therefore the amount of mechanical movements can be reduced. For instance, in 3-D space, magnetic field strength can be regarded as a vector defined by three linearly independent base vectors. Therefore, to generate a 3-D dynamic field, a system using three coils may need only to change the electrical current in each coil, and mechanical movements may not be required. The mechanical subsystem will not need to deal with the inertia of magnets or coils to generate programmed magnetic field. The control bandwidth can be improved and the safety during the operation can be enhanced.

The system is able to actuate medical robots through magnetic torque actuation, magnetic force actuation, or combination of these two actuation methods. Static or dynamic magnetic field strength such as rotating field, conical field, oscillating field, elliptical field, etc., for magnetic torque navigation and actuation can be implemented. Demanded magnetic gradient can also be generated for magnetic force actuation. Examples of medical robots that can be actuated may include magnetically navigated endoscopes, capsule endoscopes, guidewires, catheters, microrobots, nanorobots, or microrobotic swarms. The tasks performed by the medical robots may include locomotion, targeted delivery, sensing, or tissue manipulation. The mechanical platform can also actuate the mobile coils following the location of robot, to ensure the efficiency of actuation and at the same time enlarge the effective working area of the system.

The magnetic actuation technique can include a modeling, control and optimization method to calculate the optimal coil positions and generate the required magnetic field based on coil positions in real time. The optimal spatial position and pointing direction of the coil can be calculated based on the body shape, body part, other devices placed inside the working area, actuation mode of the controlled object, etc., in order to satisfy various requirements, such as avoid collision, conduct required actuation, minimize demanded current, reduce mechanical movement, etc. The mechanical platform may then actuate each coil to calculated position and orientation, and magnetic field calculation can be conducted according to the current pose of the coils. The magnetic field strength and gradient generated by each coil can be calculated through a calibrated data-driven model, and then the field strength and gradient produced by the system can be calculated through a coordinate-transformation-based method. With the control and optimization method, collision during operation process can be avoided, demanded actuation can be conducted, and on the other hand, applied electrical current can be minimized and mechanical movement of the system can be reduced.

BRIEF DESCRIPTION OF THE DRAWINGS

FIG. 4E illustrates a fifth example of a mechanical structure for a robotic arm assembly, according to some embodiments.

FIG. 4F illustrates a sixth example of a mechanical structure for a robotic arm assembly, according to some embodiments.

DETAILED DESCRIPTION

Figure 1A:
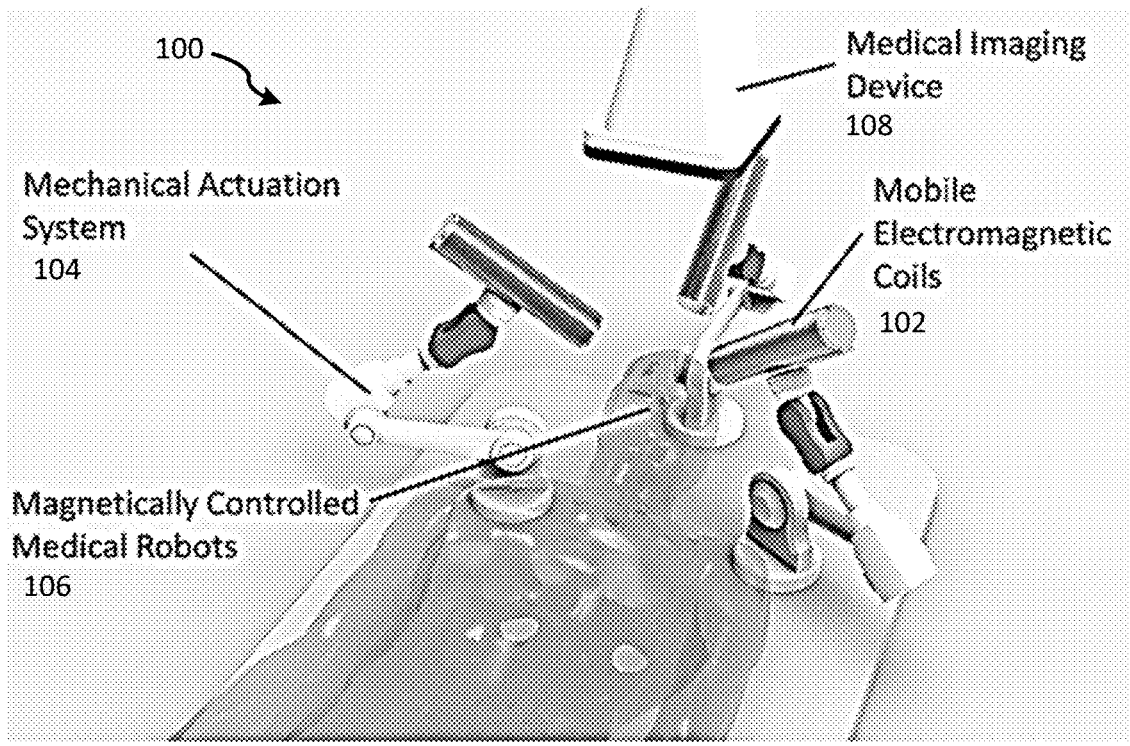
FIG. 1A illustrates an example of a magnetic actuation system according to some embodiments.

Reference will be made in detail to exemplary embodiments in the following description. The objects, characteristics, advantages and methods of the various embodiments will be more clearly understood through the drawings and following description but are by no means limited the to the drawings and following description.

One way to generate the demanded magnetic field to actuate a magnetic device is to use stationary magnetic actuation systems. The magnetic field in such systems can be generated by stationary electromagnetic coils or permanent magnets, which are usually placed at a fixed spatial location. As for electromagnetic-coil-based stationary systems, various magnetic robots, such as capsule endoscopes, magnetic catheters or microrobots, can be actuated remotely through magnetic fields that are generated by simply adjusting electric currents in each coil. As for permanent-magnet-based stationary systems, required magnetic field can be produced through changing the direction of each permanent magnets, and 5-degree-of-freedom (5-DOF) control of an object can be conducted. The merits of the stationary systems mainly lie in faster response, higher precision of generated magnetic field and capability of 5-DOF control. However, challenges will appear when scaling up the stationary systems for clinical use. For coil-based systems, enlarged workspace may require larger coils and current, which will lead to severe heat generation and reduced frequency response, and further increase the complexity of the design. For permanent-magnet-based systems, larger magnets may be required to enlarge the effective area, while the strong magnetic field that exists inside the workspace and around the device may potentially cause danger.

Using mobile magnetic actuation systems is another method to produce the required magnetic field, with the advantage of larger working area over stationary systems. Among the mobile systems, one approach is to use permanent magnet that is connected to a robotic manipulator to generate magnetic field. Such systems may implement 5-DOF manipulation, and singularity-free property. These systems can reduce or eliminate heat generation, but the strong field, which cannot be turned off, may limit the controllability and raise concerns on safety during operation. Moreover, mechanical movements will be needed for dynamic magnetic fields, and therefore, the inertia of the permanent magnet may limit the control bandwidth and variety of the generated field. The other approach is to implement mobile electromagnetic coils instead of permanent magnets. The electromagnetic coils can provide improved control bandwidth and on/off capability. The robotic system can move the electromagnetic coils within a relatively larger area to expand the working space. Some mobile-coil-based systems may implement coils with movements that are coupled with each other, which can hinder their capability to deal with the irregular obstructions that exist in the workspace during clinical applications, such as spaces needed by other medical devices, area for imaging systems and the complex surface of human body. Moreover, the limited flexibility may hinder further improvements on energy efficiency, which may be needed to reduce the heat generation and the overall size, cost and frequency response of the system.

Compared with these other systems, a magnetic actuation system with decoupled mobile coils can further improve the energy efficiency due to the enhanced flexibility. Implementation of intelligent control strategies allows the system to control the coils to avoid collisions with obstructions, and at the same time enables the system to place the coils to optimal positions in order to minimize applied current and heat generation. The flexibility of the system also makes the system compatible with fluoroscopic intraoperative imaging devices, such as C-Arm X-ray machine, for real-time localization during surgical process.

Figure 1B:
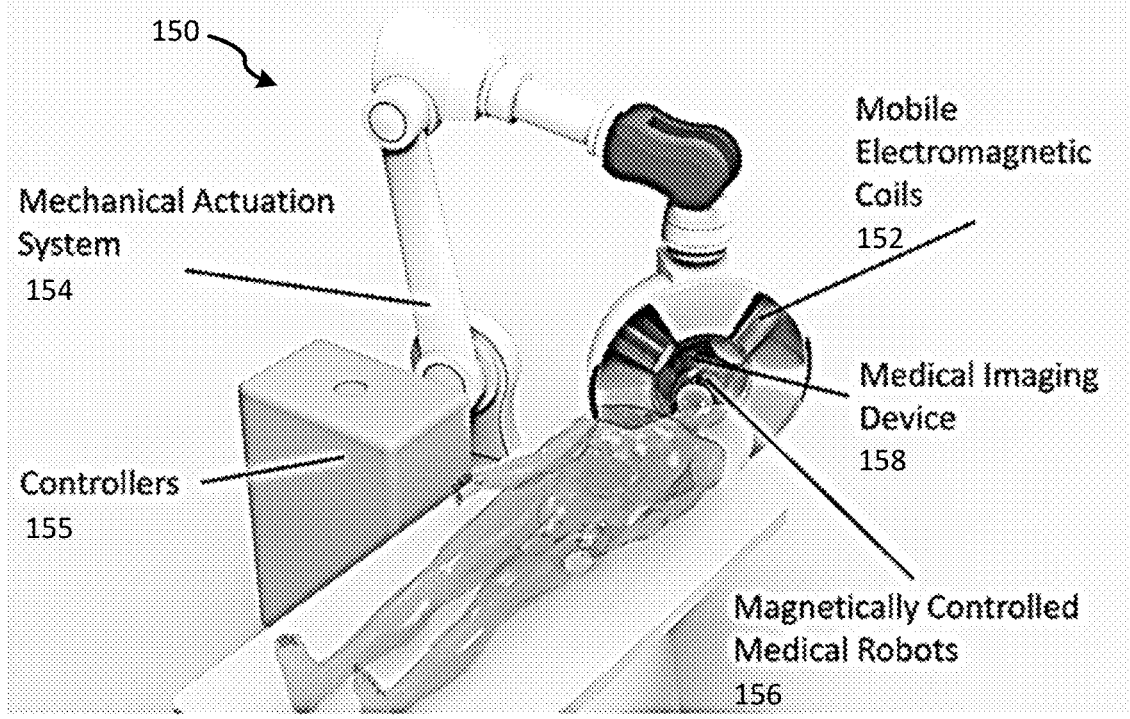
FIG. 1B illustrates another example of magnetic actuation system according to some embodiments.

FIG. 1A and FIG. 1B illustrate examples of the magnetic actuation system, according to some embodiments. The system may include multiple mobile electromagnetic coils that can be actuated individually or together by mechanical platform, such as robotic arms, to enlarge the effective workspace and improve the flexibility. Usage of electromagnetic coils makes the magnetic field able to change dynamically with a high frequency and able to be entirely switched off, which enlarge the control bandwidth, increase the variety of magnetic field, and enhance the safety during operation. Linking to the mechanical platform enables the coils to change spatial locations and orientations in pace with the locomotion of the medical robot, reach closer to patients under specific control strategies, and therefore increase the energy efficiency. As a result, smaller coils and lower current will be needed to generate required magnetic field strength. Flexibility of coils' positions and orientations also provides abundant space for medical imaging devices and other facilities to conduct real-time tracking of medical robots or other surgical process. The system can generate various demanded magnetic fields to control multiple kinds of magnetic devices including medical robots such as magnetically navigated endoscopes, capsule endoscopes, guidewires, catheters, microrobots, nanorobots, or microrobotic swarms, etc. for conducting assigned tasks such as locomotion, changing orientation, targeted delivery, biosensing, and tissue manipulation, etc. The mechanical platform may include one or more robotic arm assembly to position the electromagnetic coils into optimal positions.

FIG. 1A illustrates a magnetic actuation system 100 with a distributed mechanical platform, according to some embodiments. The magnetic actuation system 100 has a mechanical actuation system 104 that utilizes three robotic arm assemblies distributed around a workspace. In other implementations, more or less number of robotic arm assemblies can be used. The three robotic arm assemblies have respective electromagnetic coils 102 attached to one end of the corresponding robotic arm assembly. Each robotic arm assembly may include multiple rotatable joints attached to respective robotic arms to provide flexibility on positioning the electromagnetic coils 102. The robotic arm assemblies can cooperate with each other, and be positioned to generate and vary a magnetic field to actuate a magnetically controlled medical robot 106, which can be placed inside a patient being operated on. The magnetic actuation system 100 can be used with a medical imaging device 108, and motion of the robotic arm assemblies can be configured to not interfere with the medical imaging device 108.

FIG. 1B illustrates a magnetic actuation system 150 with a centralized mechanical platform, according to some embodiments. The magnetic actuation system 150 has a mechanical actuation system 154 that utilizes a single robotic arm assembly. The robotic arm assembly has multiple electromagnetic coils 152 attached to an end of the robotic arm assembly. The robotic arm assembly may include multiple rotatable joints attached to respective robotic arms to provide flexibility on positioning the electromagnetic coils 152. The robotic arm assembly can position the electromagnetic coils 152 to generate and vary a magnetic field to actuate a magnetically controlled medical robot 156, which can be placed inside a patient being operated on. The mechanical actuation system 154 may include a medical imaging device 158 disposed at an end of a robotic arm. With a centralize mechanical platform, the robotic arm assembly can be attached to a base that houses one or more controllers 155 and/or a host computer that controls the movement of the robotic arm assembly and the electrical currents applied to the electromagnetic coils 152.

Figure 2:
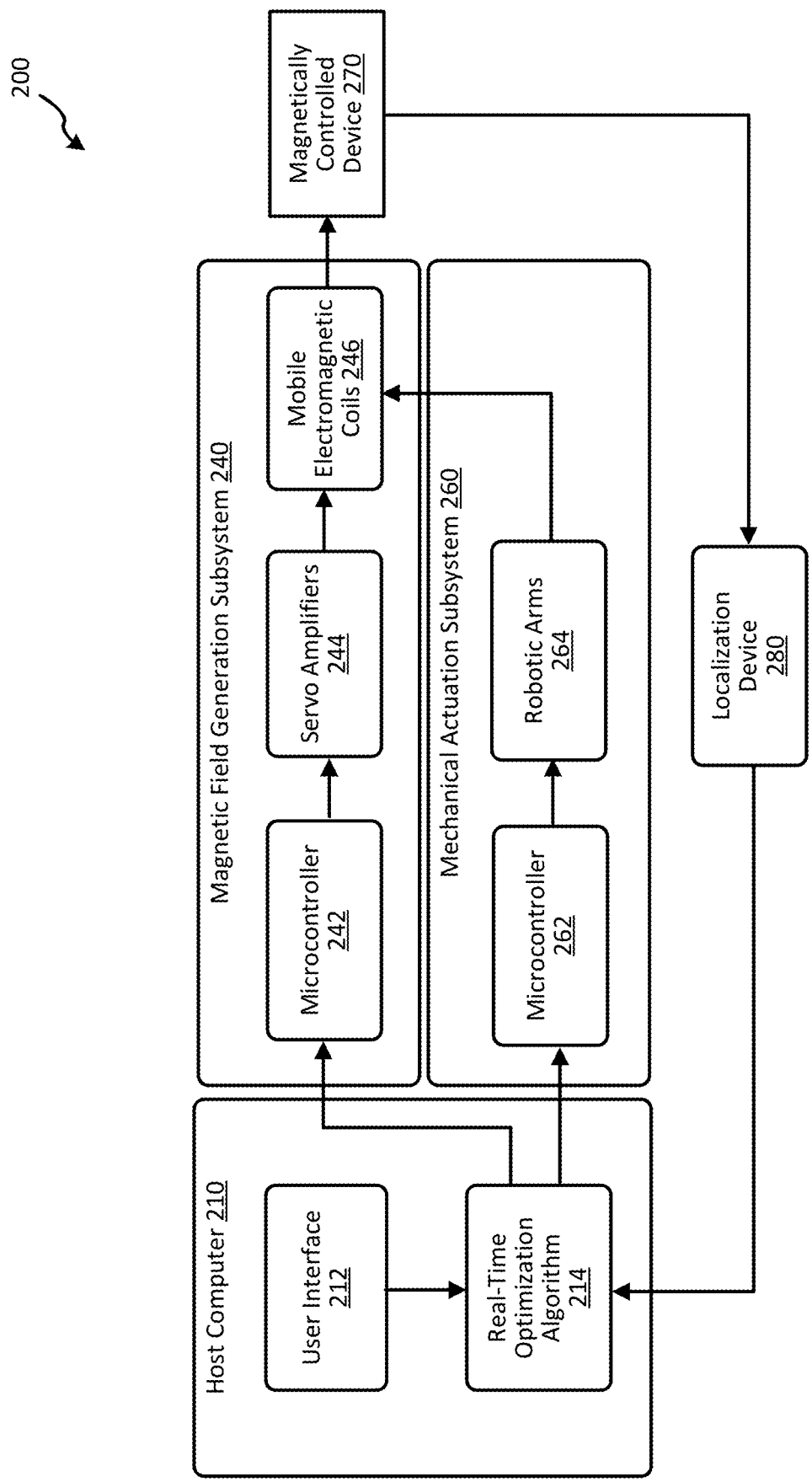
FIG. 2 illustrates a block diagram of magnetic actuation system, according to some embodiments.

FIG. 2 illustrates a block diagram of a magnetic actuation system 200, according to some embodiments. The components shown in FIG. 2 can be used, for example, to implement magnetic actuation system 100 or 150, although some implementations may omit certain components and/or include additional components not specifically shown. System 200 may include the following main structures: host computer 210, magnetic field generation subsystem 240, mechanical actuation subsystem 260, magnetically controlled device 270, and localization device 280. The host computer 210 may provide a user interface 212 for a user to input system requirements, and is in charge of conducting calculations with a real-time optimization algorithm 214 based on the user's requirements and current position of the magnetically controlled device 270. The results of the calculations including parameters of magnetic field (e.g., magnetic field strength, gradient, etc.), and the optimal positions of the coils are provided to magnetic field generation subsystem 240 and mechanical actuation subsystem 260, respectively.

In some implementations, magnetic field generation subsystem 240 may include multiple electromagnetic coils 246 configurable to generate a magnetic field to actuate a magnetically controlled device 270 disposed inside a volume of substance such as a human body. Mechanical actuation subsystem 260 may include one or more robotic arm assemblies to implement robotic arms 264 to place the electromagnetic coils 246 in respective optimized positions and orientations. Host computer 210 can be configured to implement a model of the magnetic field based on coordinate transformations between different coordinate systems including a world frame of reference, a robotic arm frame of reference corresponding to each robotic arm assembly, and a coil frame of reference for each electromagnetic coil. Host computer 210 can execute a real-time optimization algorithm 214 to determine the optimized positions and orientations of the electromagnetic coils 246 based on the model of the magnetic field, and provide the optimized positions and orientations to the mechanical actuation subsystem 260 to position the electromagnetic coils 246.

These two subsystems 240 and 260 can perform further calculations in microcontrollers to generate more detailed commands to actuators. For example, magnetic field generation subsystem 240 may include microcontroller 242 to control a set of amplifiers 244 (and/or power supplies) to apply electrical currents to the electromagnetic coils 246. For example, microcontroller 242 can generate signals that represent the required electrical currents in each mobile coil and provide the signals to amplifiers 244, and the amplifiers 244 may apply the currents to the electromagnetic coils 246 to generate the demanded magnetic field. At the same time, mechanical actuation subsystem 260 may include microcontroller 262 to control a set of motors controlling the one or more robotic arm assemblies to place the electromagnetic coils 246 in the optimized positions and orientations. For example, microcontroller 262 may calculate the angle of each joint of robotic arms in the mechanical platform. The angles calculated by microcontroller 262 are provided to robotic arms 264, and motors of the robotic arms 264 can place the coils to the demanded positions and orientations. The magnetically controlled device 270 such as a medical robot can be actuated by the magnetic field generated by the electromagnetic coils 246, and conduct the required tasks such as operating inside the body of a patient. One or more localization devices 280 can monitor the condition of magnetically controlled device 270 in real-time for position feedback and close-loop control.

In some implementations, mechanical actuation subsystem 260 may have a mechanical platform with one robotic arm assembly along with other mechanisms, or more than one robotic arm assemblies that can cooperate with each other. The mechanical platform can be made of materials with low magnetic permeability. Each robotic arm assembly can have a serial mechanical structure that consists of joints and links. The joints can conduct rotational or translational movements while the links or robotic arm segments can be rigid structure. An end point of the serial mechanical structure is fixed and the other end point is free to move. The movement of each joint will lead to the movements of the structures after the joint.

If the mechanical actuation subsystem 260 implements more than one robotic arm assembly, the robotic arm assemblies can cooperate with each other using a method that is based on the coordinate transformation between the world frame and each robotic arm assembly's frame of reference. The forward and inverse kinematics of the robotic arm assembly can be determined. For each robotic arm assembly, given the demanded position of the coil's center and orientation of the coil, the angle of the joints can be calculated.

If the mechanical actuation system 260 implements one robotic arm assembly along with other mechanisms, the modeling of the system can be done using a method based on coordinate transformation between the world frame and robotic arm assembly's frame of reference. The robotic arm actuates the mobile electromagnetic coils together to a demanded position, and the mechanism at the tip of robotic arm actuates each mobile electromagnetic coil to respective required position and orientation. The mechanism at the tip of robotic arm can be operated automatically or manually. During operation, the relative position of mobile electromagnetic coils can be adjustable or fixed.

In some implementations, localization device 280 can be placed on the robotic arm, on a table, or on the floor. The localization device 280 can be X-ray imaging devices, ultrasound imaging devices, digital camera, magnetic field sensors, photo-acoustic imaging devices, or other devices that can emits and receive electromagnetic waves. If localization device 280 is placed on robotic arm, a mechanical structure can be implemented to stretch out, retract back, or adjust the orientation of the localization device 280. A digital camera can also be placed on robotic arm as mentioned, and the camera can also be used for searching for the region-of-interest on the body which is marked by the operator.

The electromagnetic coils 246 may include a solenoid surrounding a core that is made of soft magnetic materials, and may contains structures to assist heat dissipation. The electromagnetic coils 246 may be covered by soft materials to prevent damage from possible collisions. The electromagnetic coils can be in cylindrical, cuboid, or any other shape as long as the magnetic field generated by it can be modelled. The tip of each electromagnetic coil can be flat, hemisphere, cone or frustum. The tip of the coil and the core can be a whole or separate.

Using the design shown in FIG. 2, calculations can be distributed to different parts of the system to increase speed and reduce interference. The burden of host computer 210 can be lessened to allow host computer 210 to conduct more complex computations, such as real-time optimization on coil positions, image processing, and/or control algorithms. For magnetic field generation subsystem 240, the signal of magnetic field can be calculated and produced in a high control frequency with few interruptions to produce a time-varying magnetic field suitable for actuation of the magnetically controlled device 270. In some implementations, some or all of the functionality of microcontroller 242 and/or microcontroller 262 can be integrated as part of host computer 210.

Figure 3:
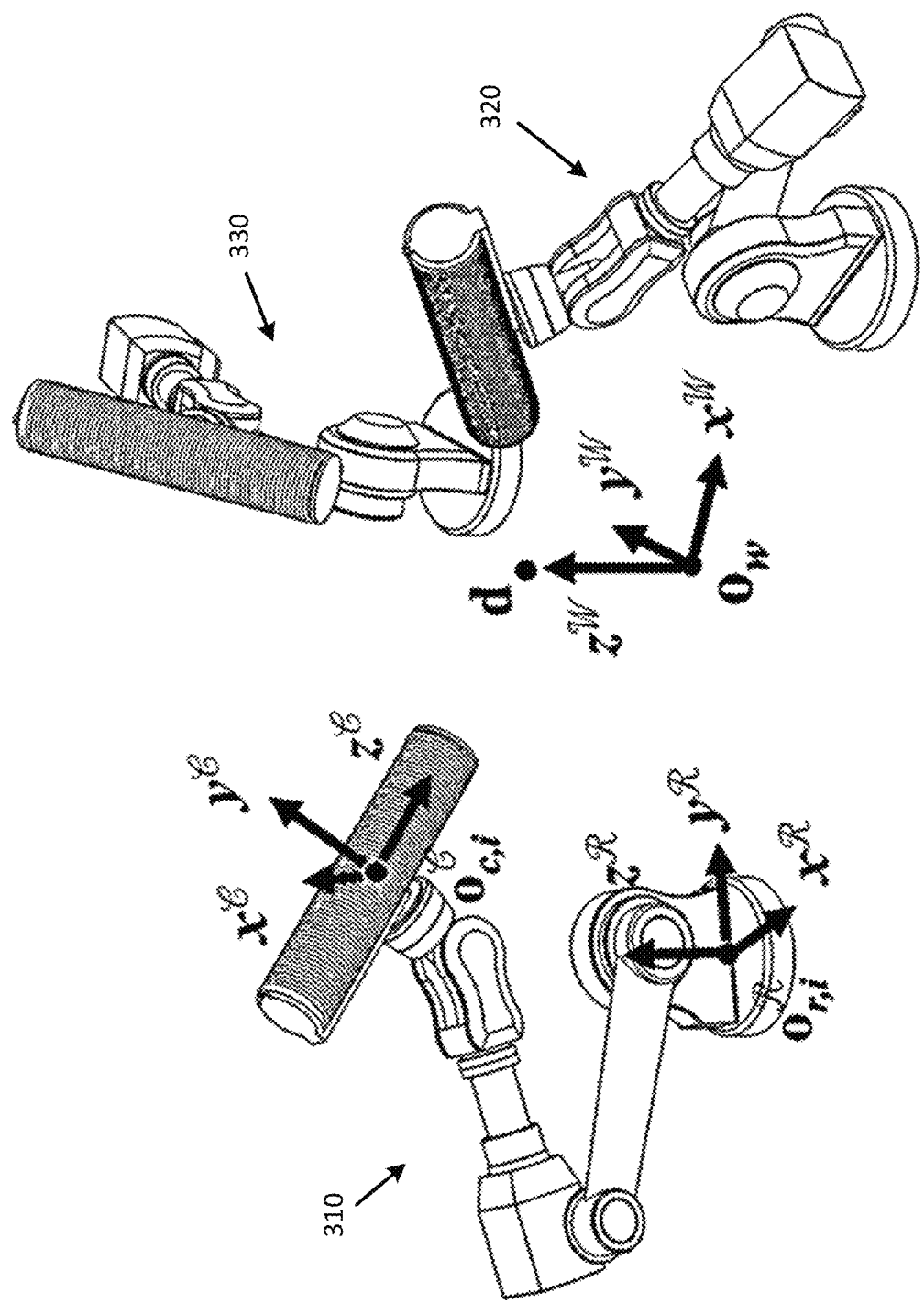
FIG. 3 illustrates the different frames of reference for system modeling, according to some embodiments.

To drive the magnetic actuation system, a model of the magnetic field can be constructed. FIG. 3 provides a drawing illustrating the different frames of reference in the system for a better understanding of the modelling technique. The system in FIG. 3 includes three robotic arm assemblies 310, 320, and 330. Assuming there exists a medical robot located at a spatial location d, and d is within the reachable area of mechanical platform. The main purpose of modeling is to make the system generate the required magnetic field strength B and magnetic force F at point d. The calculations can be conducted under three frames of reference or coordinate systems: world frame (with no superscript), robotic arm frame (with calligraphic superscript $\mathcal{R}$), and coil frame (with calligraphic superscript $\mathcal{C}$). The frames can be defined as follows. The world frame has the center of the working space as the origin, shown as $o_w$ in FIG. 3. The $i_{th}$ robotic arm's frame defines the origin as the base of each arm, shown as $\mathbf{o}_{r,i}^{\mathcal{R}}$ in FIG. 3. For the $i_{th}$ coil's frame, the origin is at the center of the coil and z axis is along the axial direction of the coil, shown as $\mathbf{o}_{c,i}^{\mathcal{C}}$ in FIG. 3. The modeling method is based on the coordinate transformation within these three frames. The model of mechanical platform is built between world frame and robotic arm frame, and modeling of a single coil is under coil frame. As for the overall magnetic field generation, the calculation is conducted between the world and coil frame. Within the description, light letters stand for scalars, bold lowercase letters stand for vectors or coordinates, and bold uppercase letters represent matrices. Magnetic field strength B and force F are still vectors but they are indicated as bold uppercase due to custom.

Figure 4A:
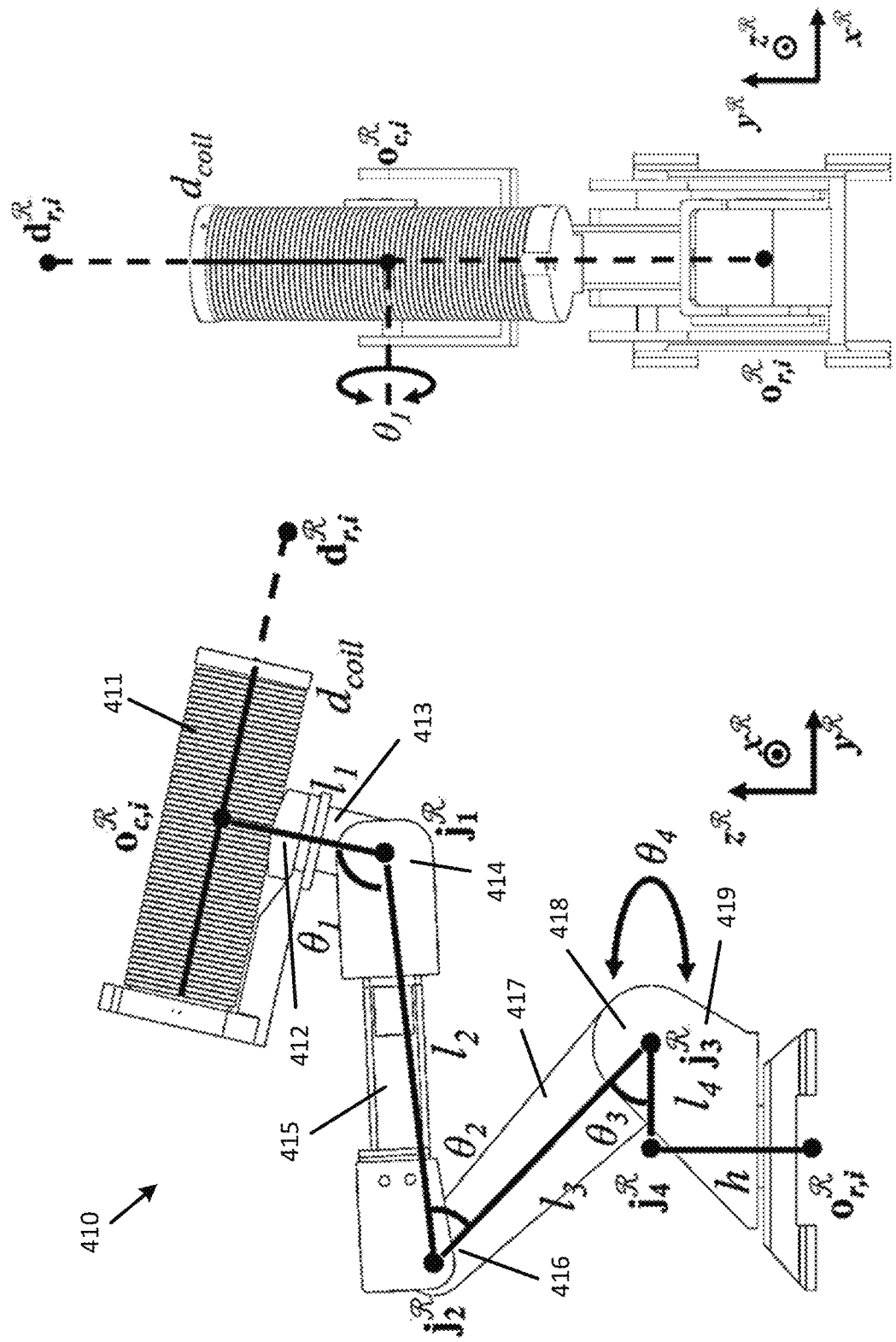
FIG. 4A illustrates a first example of a mechanical structure for a robotic arm assembly, according to some embodiments.
Figure 4B:
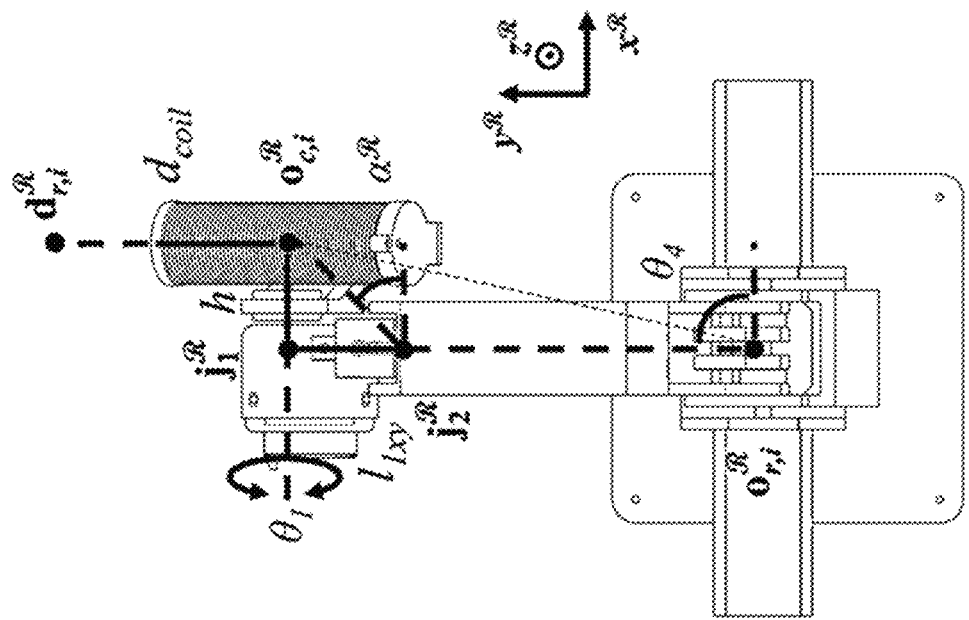
FIG. 4B illustrates a second example of a mechanical structure for a robotic arm assembly, according to some embodiments.
Figure 4B:
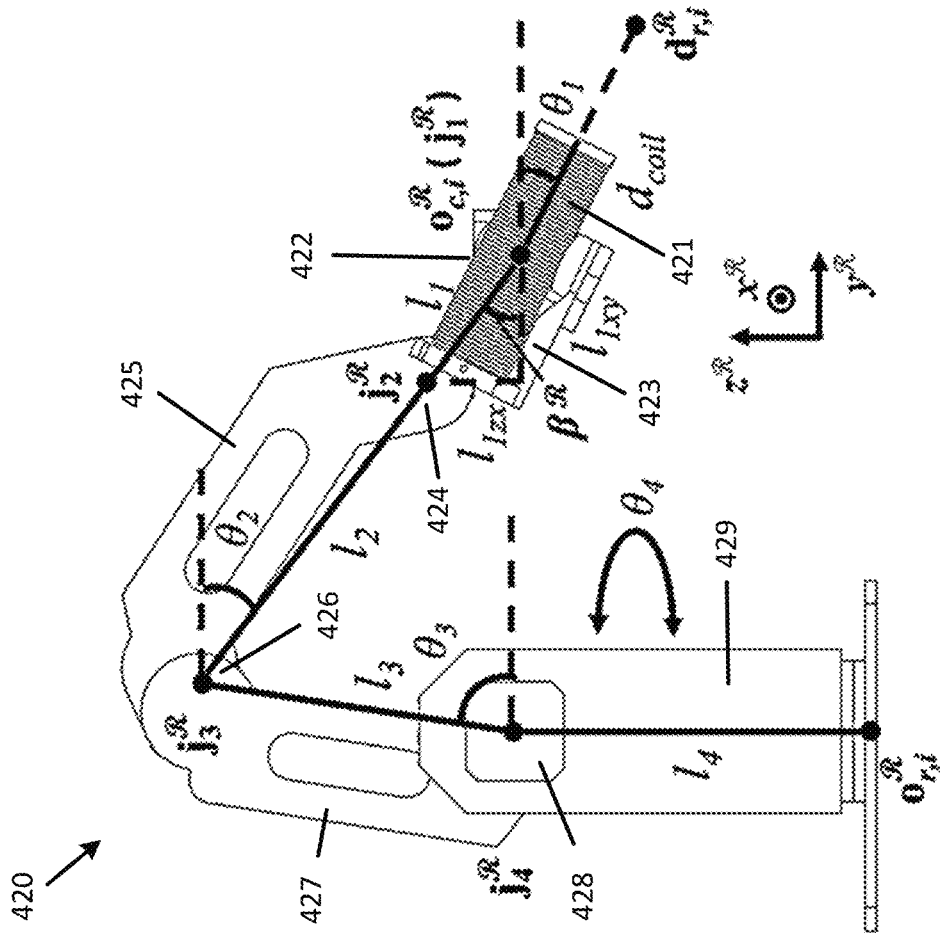
Figure 4D:
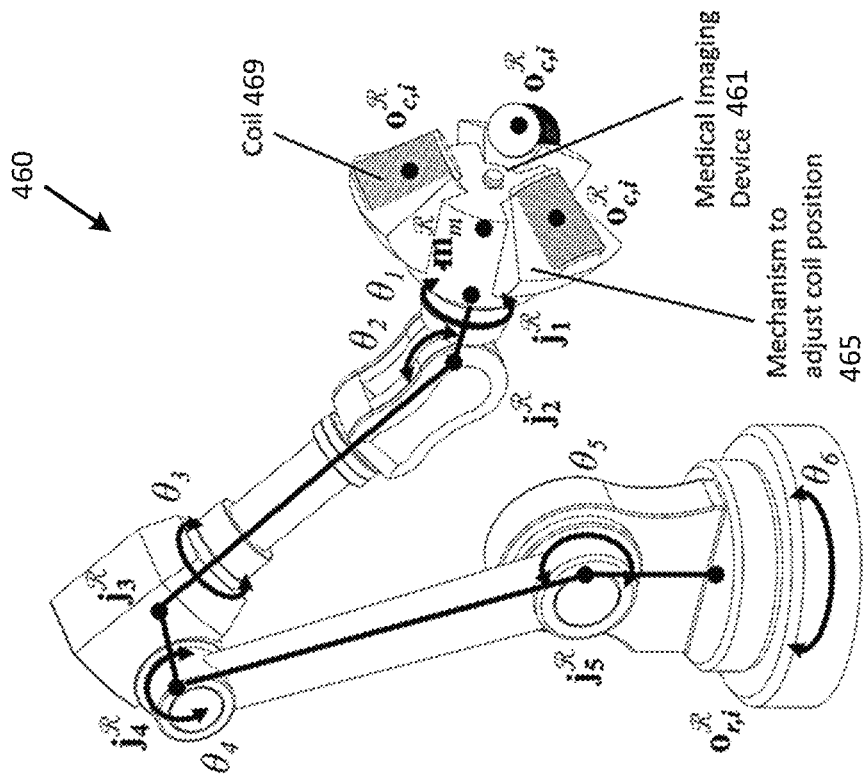
FIG. 4D illustrates a fourth example of a mechanical structure for a robotic arm assembly, according to some embodiments.
Figure 4C:
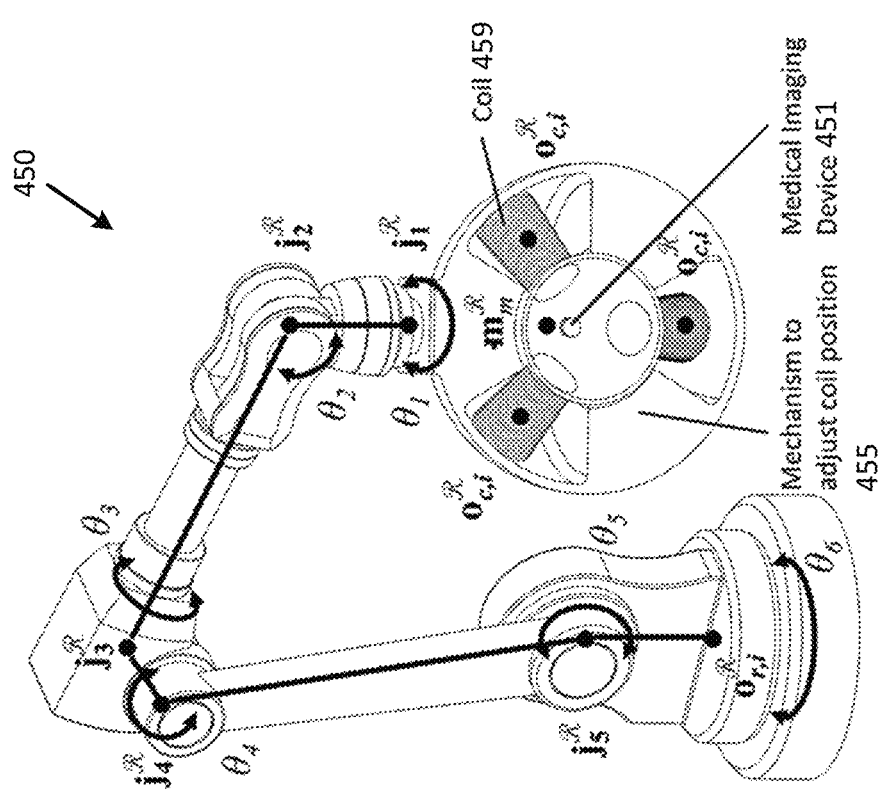
FIG. 4C illustrates a third example of a mechanical structure for a robotic arm assembly, according to some embodiments.

FIGS. 4A-F illustrate various embodiments of the mechanical structures to position the mobile electromagnetic coil. For distributed mechanical platform, the robotic arms that can be implemented are shown in FIG. 4A and FIG. 4B. The side view is on the left part and top view is on the right. For centralized mechanical platform, the robotic arms that can be implemented are shown in FIG. 4C and FIG. 4D, and the mechanism for adjusting individual coil's position can be designed as FIG. 4E or FIG. 4F. To construct the mathematical model of the above-mentioned embodiments, it's essential to convert the coordinate of targeted point from the world frame to robotic arm frame. Assuming there is a controlled object located at point d and $d = (x_d, y_d, z_d) \in \mathbb{R}^3$ is the coordinate under world frame, in order to calculate the joint angles of the robotic arms, the coordinate should be transferred to robotic arm frame, $$\mathbf{d}_i^{\mathcal{R}} = \mathbf{T}_{\mathcal{R},i}^{\mathcal{W}} \cdot d + \mathbf{t}_{\mathcal{R},i}^{\mathcal{W}} \tag{1}$$

where $\mathbf{d}_i^{\mathcal{R}} = (x_d^{\mathcal{R}}, y_d^{\mathcal{R}}, z_d^{\mathcal{R}}) \in \mathbb{R}^3$ is the coordinate of controlled object under the $i_{th}$ robotic arm coordinate system, and $\mathbf{T}_{\mathcal{R},i}^{\mathcal{W}}$ represents the rotation between the robotic arm frame and world frame and $\mathbf{t}_{\mathcal{R},i}^{\mathcal{W}}$ represents the translational movement. With this step of calculation, the position of the device under the world frame will be transformed to the frame of the $i_{th}$ robotic arm, so that each robotic arm will be able to calculate demanded joint angles, and as for distributed mechanical platform, cooperation between multiple robotic arms can be achieved.

As for the embodiment shown as FIG. 4A, the robotic arm assembly 410 may include four rotatable joints that can rotate around their respective axis and rigid structures. For example, robotic arm assembly 410 may include a first rotatable joint 412 attached to an electromagnetic coil 411. The first rotatable joint 412 can be coupled to a second rotatable joint 414 through a first robotic arm segment 413. The second rotatable joint 414 can be coupled to a third rotatable joint 416 through a second robotic arm segment 415. The third rotatable joint 416 can be coupled to a fourth rotatable joint 418 through a third robotic arm segment 417. The fourth rotatable joint 418 can be coupled to a base through a fourth robotic arm segment 419. In some implementations, one rotatable joint 412 can rotate in horizontal plane and the other three rotatable joints 414, 416, and 418 can rotate in a same vertical plane. The mobile electromagnetic coil is fixed at the end of the fourth plane that movement of any joint will change the position or orientation of the coil 411.

The analytical model of the inverse kinematics can be built through the following calculations. Point $\mathbf{o}_{c,i}^{\mathcal{R}} = (x_{oc}^{\mathcal{R}}, y_{oc}^{\mathcal{R}}, z_{oc}^{\mathcal{R}}) \in \mathbb{R}^3$ is the center of the $i_{th}$ coil under robotic arm frame, and $\mathbf{j}_1^{\mathcal{R}}$, $\mathbf{j}_2^{\mathcal{R}}$, $\mathbf{j}_3^{\mathcal{R}}$ and $\mathbf{j}_4^{\mathcal{R}}$ are four parts of the robotic arm. The value of $\mathbf{o}_{c,i}^{\mathcal{R}}$ can be generated from the optimization process or be determined by manually defined rules, for example, the robot is always kept at the axial direction of the coil, and the tilting angle of the coil α and distance between the coil's center and the robot $d_{coil}$ can be assigned. By calculating the coordinates of joints, the required angles, $\theta_1$, $\theta_2$, $\theta_3$, and $\theta_4$, will be determined. As the first step, the base motor of robotic arm should align the upper part of the arm to the direction of the controlled target $d_i^R$, so the angle $\theta_4$ can be calculated as following.

$$\theta_4 = \tan^{-1}\frac{x_{oc}^R}{y_{oc}^R} \qquad (2)$$

For the next step, as all the points are within the same plane after the base turns to the correct direction, the calculation of the joints $j_1^R$ to $j_3^R$ can be conducted in a 2-D space. The 2-D coordinates of $j_1^R=(m_{j1}, n_{j1})$, $j_2^R=(m_{j2}, n_{j2})$ and $j_3^R=(m_{j3}, n_{j3})$ on plane $\{j_1^R j_2^R j_3^R\}$ can be calculated, and therefore, the angle of $\theta_1$ to $\theta_3$ is able to be determined as $$\theta_1 = \cos^{-1}\left(\frac{l_1^2 + l_2^2 - \|\overline{o_{c,i}^R j_2^R}\|^2)^2}{2l_1 l_2}\right) \qquad (3)$$

$$\theta_2 = \cos^{-1}\left(\frac{l_2^2 + l_3^2 - \|\overline{j_1^R j_3^R}\|^2}{2l_1 l_3}\right) \qquad (4)$$

$$\theta_3 = \pi - \tan^{-1}\left(\frac{z_{oc}^R - l_1\cos\alpha - h}{m_{j1} - l_4}\right) - \cos^{-1}\left(\frac{l_3^2 + \|\overline{j_1^R j_3^R}\|^2 - l_2^2}{2l_3\|\overline{j_1^R j_3^R}\|}\right) \qquad (5)$$

where the characters with overline is the vector from one point to another, e.g. $\overline{j_1^R j_3^R}$ is the vector from joint $j_1^R$ to $j_3^R$. The calculation process built the analytical model for the inverse kinematics, which can improve the calculation speed compared with non-analytical models. With the above angles, the motors on each robotic arm are able to position the mobile electromagnetic coils to demanded positions and orientations.

Another embodiment of a robotic arm assembly used for distributed mechanical platform is illustrated in FIG. 4B. This embodiment includes at least four rotatable joints. For example, robotic arm assembly 420 may include a first rotatable joint 422 attached to an electromagnetic coil 421. The first rotatable joint 422 can be coupled to a second rotatable joint 424 through a first robotic arm segment 423. The second rotatable joint 424 can be coupled to a third rotatable joint 426 through a second robotic arm segment 425. The third rotatable joint 426 can be coupled to a fourth rotatable joint 428 through a third robotic arm segment 427. The fourth rotatable joint 428 can be coupled to a base through a fourth robotic arm segment 429. In some implementations, one rotatable joint rotates on horizontal plane and the other three rotate in vertical plane. The rotating planes of the vertical joints can be different. The value of $o_{c,i}^R$ can be determined by the same method as in the first embodiment.

The forward kinematics of this embodiment can be calculated as following. As shown in the FIG. 4B, $l_j$ (j=1, 2, 3, 4) stands for the length of the $j_{th}$ link. Because of the inherent feature of the robot arm, link 3 and link 2 are parallel-connected s.t changes of $\theta_3$ would not change $\theta_2$. The orientation of the coil is controlled by $\theta_1$ and $\theta_4$ and position of the center point of the coil $o_{c,i}^R$ is controlled by $\theta_2$, $\theta_3$ and $\theta_4$. Consequently, we could break down the 5 degrees of freedom of the robot arm into two categories.

$$\begin{bmatrix} POS(o_{c,i}^R) \\ ORI(o_{c,i}^R) \end{bmatrix} = \begin{bmatrix} q_1(\theta_2, \theta_3, \theta_4) \\ q_2(\theta_1, \theta_4) \end{bmatrix} \qquad (6)$$

where $\theta_j$ (j=1, 2, 3, 4) represents the joint angle of $j_{th}$ motor. $\alpha^R$ is the angle between $x^R$ axis and the projection of the line that connects $o_{c,i}^R$ and $j_2^R$ on $x^R$-$y^R$ plane. $\beta^R$ is the angle between $l_1$ and $x^R$-$y^R$ plane, and is constant because of e par el feature of the robot arm. Their values are:

$$\alpha^R = \theta_4 - \tan^{-1}\left(\frac{h}{l_{1xy}}\right) \qquad (7)$$

$$\beta^R = \tan^{-1}\left(\frac{l_{1z}}{l_{1xy}}\right) \qquad (8)$$

The offset vector $\overline{o_{c,i}^R j_2^R}$ is a vector that points from $o_{c,i}^R$ to $j_2^R$, and can be derived as $$\overline{o_{C,I}^R j_2^R} = \begin{bmatrix} \cos\alpha^R \sqrt{h^2 + l_{1xy}^2} \\ \sin\alpha^{iR} \sqrt{h^2 + l_{1xy}^2} \\ l_1 \sin\beta^R \end{bmatrix} \qquad (9)$$

Position of $j_2^R$ can be analytically derived as $$j_2^R = \begin{bmatrix} \sin\theta_1(l_2\cos\theta_2 + l_3\cos\theta_3) \\ \cos\theta_1(l_2\cos\theta_2 + l_3\cos\theta_3) \\ l_3\sin\theta_3 - l_2\sin\theta_2 + l_4 \end{bmatrix} \qquad (10)$$

Then the position of the center of $o_{c,i}^R$ can be attained as $$POS(o_{c,i}^R) = q_1(\theta_2, \theta_3, \theta_4) = \overline{o_{c,i}^R j_2^R} + j_2^R \qquad (11)$$

Assuming $rotx(\theta_1)$ and $rotz(\theta_4)$ are the rotation matrix around $x^R$ and $z^R$ axis respectively, the orientation of the $i_{th}$ coil can be calculated as following.

$$ORI(o_{c,i}^R) = r_{c,i}^R = q_2(\theta_1, \theta_4) = rotx(\theta_1) \times rotz(\theta_4) \times \begin{bmatrix} 1 \\ 0 \\ 0 \end{bmatrix} \qquad (12)$$

The inverse kinematics of the embodiment is derived in the following process. Because of the parallel connected joints of the robot arm, 5 degrees of freedom can be decoupled, and thus analytical solution of the inverse kinematics can be calculated.

$$\theta_4 = \tan^{-1}\left(\frac{y_{c,i}^R}{x_{c,i}^R}\right) + \tan^{-1}\left(\frac{h}{r}\right) \qquad (13)$$

where $x_{c,i}^R$ and $y_{c,i}^R$ are the x and y coordinates of $o_{c,i}^R$ respectively, and r is defined as following.

$$r = (x_{c,i}^R)^2 + (y_{c,i}^R)^2 - h^2 \qquad (14)$$

From forward kinematics, $\theta_1$, $\theta_2$, $\theta_3$ can be derived as $$s = \cos^{-1}\left(\frac{(r - l_{1xy})^2 - (z_{c,i}^R - l_1)^2 - l_2^2 - l_3^2}{2l_2 l_3}\right) \quad (15)$$

$$\theta_2 = \sin^{-1}\left(\frac{l_3 \sin(\pi - s)}{\sqrt{(r - l_{1xy})^2 - (z_{c,i}^R - l_1)^2}}\right) - \tan^{-1}\left(\frac{z_{c,i}^R - l_1}{r - l_{1xy}}\right) \quad (16)$$

$$\theta_3 = s - \theta_2 \quad (17)$$

$$\theta_1 = \tan^{-1}\left(\frac{y_r^R}{x_r^R}\right) \quad (18)$$

where $y_r^R$ and $z_r^R$ is the y coordinate and z coordinate of $r_{ci}^R$ respectively.

As for centralized mechanical platform, one robotic arm is implemented and a mechanism is connected to the end of the robotic arm to adjust position and orientation of each individual mobile coil. The center of the mechanism locates at $m_m^R$ and the orientation of the mechanism is $o_m^R$. The robotic arm is in charge of actuating the mechanism to required location and orientation, and then the position and orientation of each individual coil can be adjusted by the mechanism manually or automatically. Two embodiments are shown as FIG. 4C and FIG. 4D respectively. As for the embodiment shown in FIG. 4C, the orientation of the mechanism $o_m^R$ is orthogonal to the last link $\overline{j_1 j_2}$, of the robotic arm assembly 450, and rotation of the last joint $j_1$ will change the value of $\theta_1$ and therefore change the orientation of the mechanism 455 at the end of robotic arm. For the embodiment in FIG. 4D, the orientation $o_m^R$ of the mechanism 465 is parallel to the last link $\overline{j_1 j_2}$ of the robotic arm assembly 460. Changing $\theta_1$ will not change the orientation of the mechanism 465, but may change the pose of the mobile coils 469.

Two designs of the mechanism that can be used to implement mechanism 455 and/or 465 to adjust position and orientation of each coil are shown as FIG. 4E and FIG. 4F. In FIG. 4E, structure 470 includes a track 477, a slider 475, and a scissor linkage 471 is implemented to adjust the pose of coil 479. The track 477 is connected to the robotic arm and by changing the distance $l_m$ between the slider 475 and the end of the track 477, the orientation and the spatial position of the coil 479 can be adjusted. In FIG. 4F, structure 480 includes two telescopic structures 481, and by changing the length of $l_{m1}$ and $l_{m2}$, the pose of coil 489 can be adjusted. The mechanism can be adjusted manually or automatically according to the different requirements in real applications. When a manual mechanism is implemented, sensors can be used to monitor the pose of the coil for calculation of magnetic field. Besides, a simple fixed frame may also be implemented as the mechanism if the coils' positions and orientations don't demand adjustment during operation. For centralized mechanical platform, medical imaging devices and sensors can be implemented for localization of robots. On one hand, for medical imaging devices or sensors with a probe-like structure, such as ultrasound or camera, the device can be placed at the end of robotic arm, see the place marked 451 and 461 in FIG. 4C and FIG. 4D respectively, as an "eye-in-hand" design. On the other hand, as for medical imaging devices or sensors that are bulky and requires a wide area to work, such as computed tomography (CT) or X-ray imaging system, they can be placed separately with the system. Furthermore, when a camera is implemented on this design, another function can be realized. The operators can mark a region of interest on the body, and then the system can search for the mark through camera and actuate the coils to the demanded region.

In order to generate the demanded magnetic field at a specific point where the controlled device locates, an algorithm based on coordinate transformation and linear superposition can be implemented. For a magnetic medical robot at position $d=(x_d, y_d, z_d)$ under world frame, the relative position with the $i_{th}$ coil can be calculated to obtain the magnetic field that is generated by this coil. Therefore, coordinate transformation between the world frame and the $i_{th}$ coil's frame is used. Assuming the orientation of the $i_{th}$ coil can be expressed using unit vector $r_{c,i}=(x_{ri}, y_{ri}, z_{ri})$, and the position of the origin of the coil frame under world frame is $o_{c,i}$, the rotation matrix $T_W^C$ and translational vector $t_W^C$ or coordinate transformation from world frame to the $i_{th}$ coil's frame can be calculated through following equations:

$$\alpha_{c,i} = \tan^{-1}\left(\frac{y_{ri}}{x_{ri}}\right) \quad (19)$$

$$\beta_{c,i} = \tan^{-1}\left(\frac{z_{ri}}{\sqrt{x_{ri}^2 + y_{ri}^2}}\right) \quad (20)$$

$$T_W^C = \begin{bmatrix} \cos\alpha_{c,i}\sin\beta_{c,i} & \sin\alpha_{c,i}\sin\beta_{c,i} & -\cos\beta_{c,i} \\ -\sin\alpha_{c,i} & \cos\alpha_{c,i} & 0 \\ \cos\alpha_{c,i}\cos\beta_{c,i} & \sin\alpha_{c,i}\cos\beta_{c,i} & \sin\beta_{c,i} \end{bmatrix} \quad (21)$$

$$t_W^C = -T_W^C o_{c,i} \quad (22)$$

With the rotational movement $T_W^C$ and translational movement $t_W^C$, the coordinate of the medical robot under world frame d can be translated to $i_{th}$ coil's frame, as $d_i^c$.

$$d_i^c = T_W^C d + t_W^C \quad (23)$$

Figure 5A:
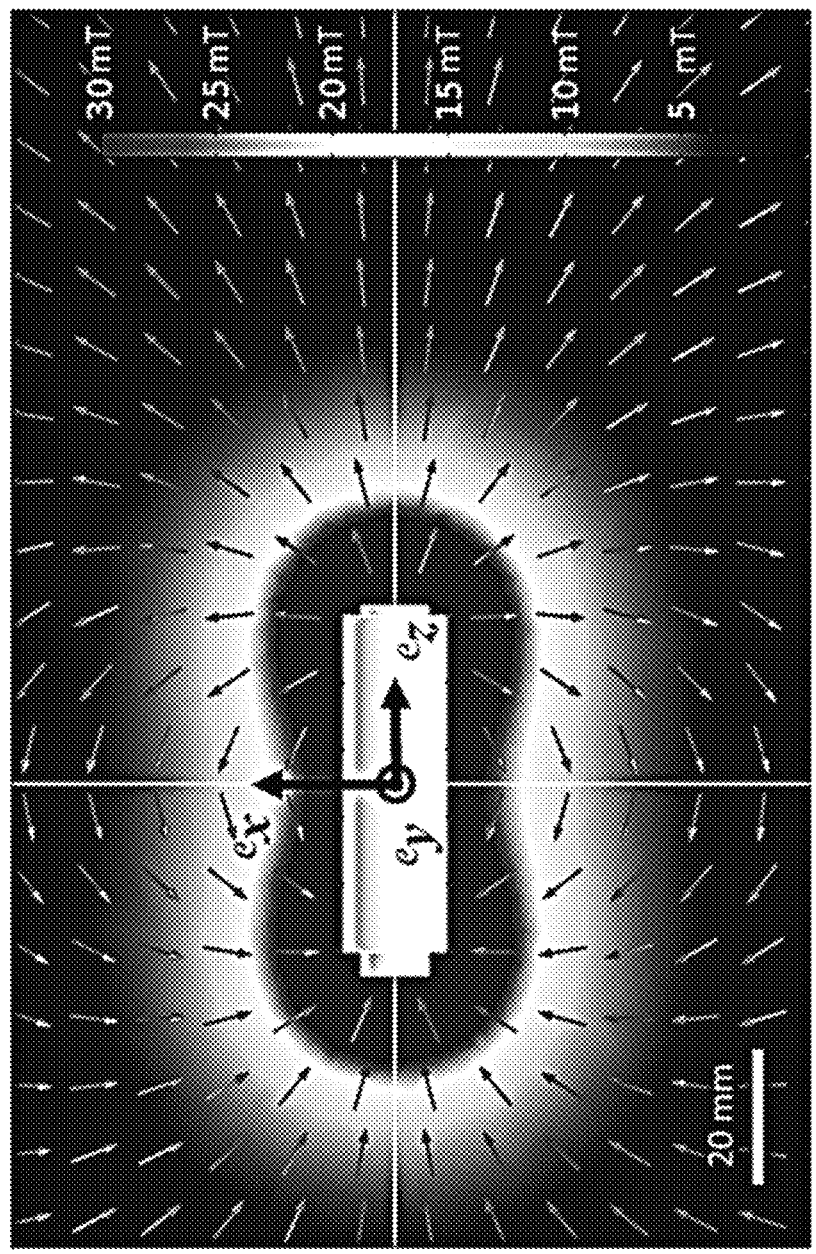
FIG. 5A illustrates an example of a magnetic field map of a single coil, according to some embodiments.
Figure 5B:
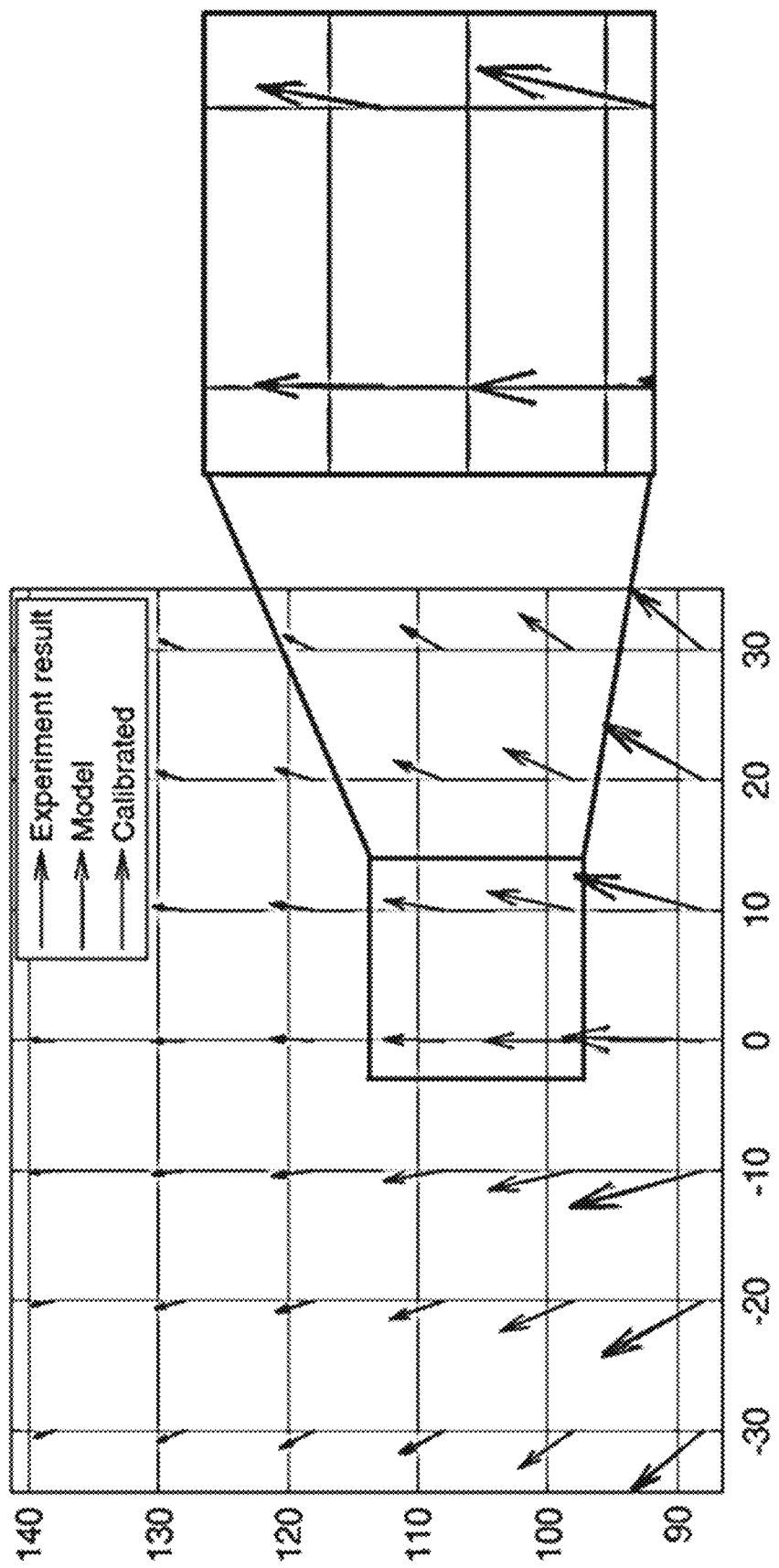
FIG. 5B illustrates an example of the calibration result of the data-driven model, according to some embodiments.

Under coil's frame, the magnetic field at point $d_i^c$ can be calculated through the following method. A field map for an electromagnetic coil with soft magnetic core and the definition of coil's frame are shown in FIG. 5A. The axial direction of the coil is defined as the z-axis of the coil frame, and x and y axis are determined according to right-hand rule. The field map is calculated through finite element method (FEM) and is data-based, and it can be seen as the simulation result of the magnetic field of a known coil, expressed $\tilde{B}_{m,i}^c$. In some implementations, the FEM results may be subject to correction before being used as the coil's model because there can be a discrepancy between the result and the real situation. So, calibrations can be conducted to correct the FEM result according to the experimental measurement of the $i_{th}$ coil's magnetic field. As for coil calibration, a calibration algorithm in three-dimensional space can be performed. The algorithm is illustrated by the following equation.

$$\tilde{B}_i^c(d_i^c) = (\lambda + \rho \cdot \| d_i^c \|^\varepsilon)^T \tilde{B}_{m,i}^c(d_i^c) \quad (24)$$

where $d_i^c$ is the coordinate of working point under the $i_{th}$ coil frame, $\tilde{B}_{m,i}^c(d_i^c)$ is the calculated magnetic field through simulation model at point $d_i^c$, and $\tilde{B}_i^c(d_i^c)$ is the calibrated field strength at $d_i^c$. $\lambda \in \mathbb{R}^{3 \times 1}$, $\rho = \text{diag}(\rho_1, \rho_2, \rho_3)$ and $\varepsilon \in \mathbb{R}$ are parameters to be determined from calibration process. The calibration result can be seen from FIG. 5B and the error on magnetic field strength norm can be reduced to an acceptable range. The calibrated magnetic strength can be implemented as the model of the $i_{th}$ coil and saved as a look-up table for quick reference. This data-driven model avoided the non-linearity of the analytical model, increased the accuracy compared with the widely-used dipole-point model and improved calculation speed. The magnetic field strength $\mathbf{B}_i^C$ that is generated by the $i_{th}$ coil at the working point $\mathbf{d}_i^C$ with a current of $I_i=1$ A can be searched and calculated from the data-driven model of the coil. The field strength will be transformed to world frame through following method.

$$B_i|_{I_i=1} = (\mathbf{T}_W^C)^{-1} \mathbf{B}_i^C |_{I_i=1} \qquad (25)$$

In this equation, $B_i|_{I_i=1}$ (i=1, . . . , n) is the magnetic field strength at point d under world frame when an $I_i=1$ A current is applied to the coil. As for a required magnetic field B, it can be regarded as the linear superposition of the fields that are generated by three coils, and $B_i|_{I_i=1}$ (i=1, . . . , n) can be considered as the base vectors. Therefore, the currents in each coil $I_i$ that is demanded to generate B can be determined by solving the following equation.

$$B = \Sigma_{i=1}^n (B_i|_{I_i=1}) \qquad (26)$$

When the base vectors $B_i|_{I_i=1}$ (i=1, . . . , n) are linear independent, any required magnetic field can be generated. Furthermore, with this method, a dynamically changed magnetic field B(t) can also be generated by applying dynamic currents IL(t) in the coils, to need the various demands for magnetic torque actuation of medical robots.

As for magnetic force actuation, the required currents in each coil can be calculated through the following method, given a demanded magnetic force F. Based on the model of magnetic field strength, magnetic force at point $\mathbf{d}_i^C$ under $i_{th}$ coil's frame is able to be calculated through the derivative of the magnetic field in Equation (11)

$$F_i^C(d_i^C) = (m_d^C \cdot \nabla) B_i^C(d_i^C) = \qquad (27)$$

$$\begin{bmatrix} \frac{\partial B_x^C}{\partial x} & \frac{\partial B_x^C}{\partial y} & \frac{\partial B_{c,x}^C}{\partial z} \\ \frac{\partial B_y^C}{\partial x} & \frac{\partial B_y^C}{\partial y} & \frac{\partial B_y^C}{\partial z} \\ \frac{\partial B_z^C}{\partial x} & \frac{\partial B_z^C}{\partial y} & \frac{\partial B_z^C}{\partial z} \end{bmatrix} \begin{bmatrix} m_{dx}^C \\ m_{dy}^C \\ m_{dz}^C \end{bmatrix} = G_i^C m_d^C$$

where $\mathbf{m}_d^C = [m_{dx}^C, m_{dy}^C, m_{dz}^C]^T$ is the dipole moment of the controlled medical robot under the $i_{th}$ coil's frame, and $G_i^C$ is the magnetic field gradient on x, y and z direction of the coil's frame at the location of the controlled object $\mathbf{d}_i^C$. Using the method that is similar to the modeling of magnetic field strength, the magnetic force generated by the $i_{th}$ coil when $I_i=1$ A can be calculated, $$F_i|_{I_i=1} = (T_W^C)^{-1} F_i^C |_{I_i=1} \qquad (28)$$
$$= (T_W^C)^{-1} G_i^C m_d^C = (T_W^C)^{-1} G_i^C T_W^C m_d$$

where $m_d$ is the dipole moment of controlled object under world frame, which is considered to be in the same direction as the generated magnetic field. Afterwards, the required current in each coil $I_i$ for a demanded magnetic force F can be acquired by solving the following equation.

$$F = \Sigma_{i=1}^n I_i (F_i|_{I_i=1}) \qquad (29)$$

In some implementations, a collision detection algorithm can be employed to prevent possible collision between the mobile electromagnetic coils with the environmental barriers inside the workspace or working area of the system, such as patient's body, other medical facilities or devices, or imaging devices for localization, etc. Assume the $i_{th}$ mobile coil is placed at position $o_{c,i}$, and the orientation is $r_{c,i}$. $q_i$ is a point that locates on the outer surface of the $i_{th}$ mobile electromagnetic coil (i=1, . . . , n) at which collision between the coil and barriers may easily happen. To conduct further calculation, the environmental barrier can be saved as a 3D model that is able to be defined by J triangles in space, and the coordinate of three vertices of each triangle are represented as $v0_j$, $v1_j$ and $v2_j$, (j=1, . . . , J). Here we define $\overrightarrow{q_i o_{c,i}}$ is a vector pointing from point $q_i$ to the origin of the $i_{th}$ coil's frame $o_{c,i}$. Vectors $\overrightarrow{v1_j v0_j}$ and $\overrightarrow{v2_j v0_j}$ are defined similarly, and they determine a plane $\{v0_j v1_j v2_j\}$ on which the $j_{th}$ triangle locates. Vector $e(\overrightarrow{q_i o_{c,i}})$ is a unit vector that originate from $q_i$ and is in the same direction $\overrightarrow{q_i o_{c,i}}$. For every triangle that constitute the 3D model of environmental barrier, $t_j$, $u_j$ and $v_j$ should be solved from the following equation.

$$\left[ -e(\overrightarrow{q_i o_{c,i}}), \overrightarrow{v1_j v0_j}, \overrightarrow{v2_j v0_j} \right] \begin{bmatrix} t_j \\ u_j \\ v_j \end{bmatrix} = o_{c,i} - v0_j (j=1, \ldots J) \qquad (30)$$

In the equation, $t_j$ is the distance between $q_i$ and the intersection point on plane $\{v0_j v1_j v2_j\}$. $u_j$ and $v_j$ are the barycentric coordinates of the intersection point. If $t_j \geq 0$, $u_j \geq 0$, $v_j \geq 0$, and $u_j + v_j \leq 1$, and the intersection point is on the same direction with vector $\overrightarrow{q_i o_{c,i}}$ and it's located inside triangle j. Therefore, a conclusion can be made that a ray $t_j \overrightarrow{q_i o_{c,i}}$ that originate from $q_i$ and in the direction of $\overrightarrow{q_i o_{c,i}}$ intersects with triangle j. Considering the 3D barrier that consists of J triangles, if there exists a triangle j' that has intersection with ray $t \overrightarrow{q_i o_{c,i}}$, $t \geq 0$, $t \in \mathbb{R}$, then collision between the electromagnetic coil and the barrier will happen. Overall, the process can be expressed in the equation.

$$Q(o_{c,i}, r_{c,i}) = \qquad (31)$$
$$\begin{cases} 1 \ (\exists j \in [1, J], \text{ so that } t_j \leq 0 \wedge u_j \geq 0 \wedge v_j \geq 0 \wedge u_j + v_j \leq 1 \text{ is true}) \\ 0 \ (\forall j \in [1, J], \text{ we have } t_j \leq 0 \wedge u_j \geq 0 \wedge v_j \geq 0 \wedge u_j + v_j \leq 1 \text{ is false}) \end{cases}$$

Here, $Q(o_{c,i}, r_{c,i})$ is the result of collision detection when a mobile electromagnetic coil is placed at location $o_{c,i}$ and orientation $r_{c,i}$.

Based on the inverse calculation methods for magnetic field strength and magnetic force that are introduced above, an optimization on the electromagnetic coil's positions and orientations can be conducted for various purposes, such as avoid collision between the coils and environmental barriers, conduct required actuation, minimize demanded current, reduce mechanical movement, etc. The optimization process is carried out during the operation of the system and through the optimization, the optimal position $\hat{o}_{c,i}$ and orientation $\hat{r}_{c,i}$ of the each coil can be calculated.

Figure 6:
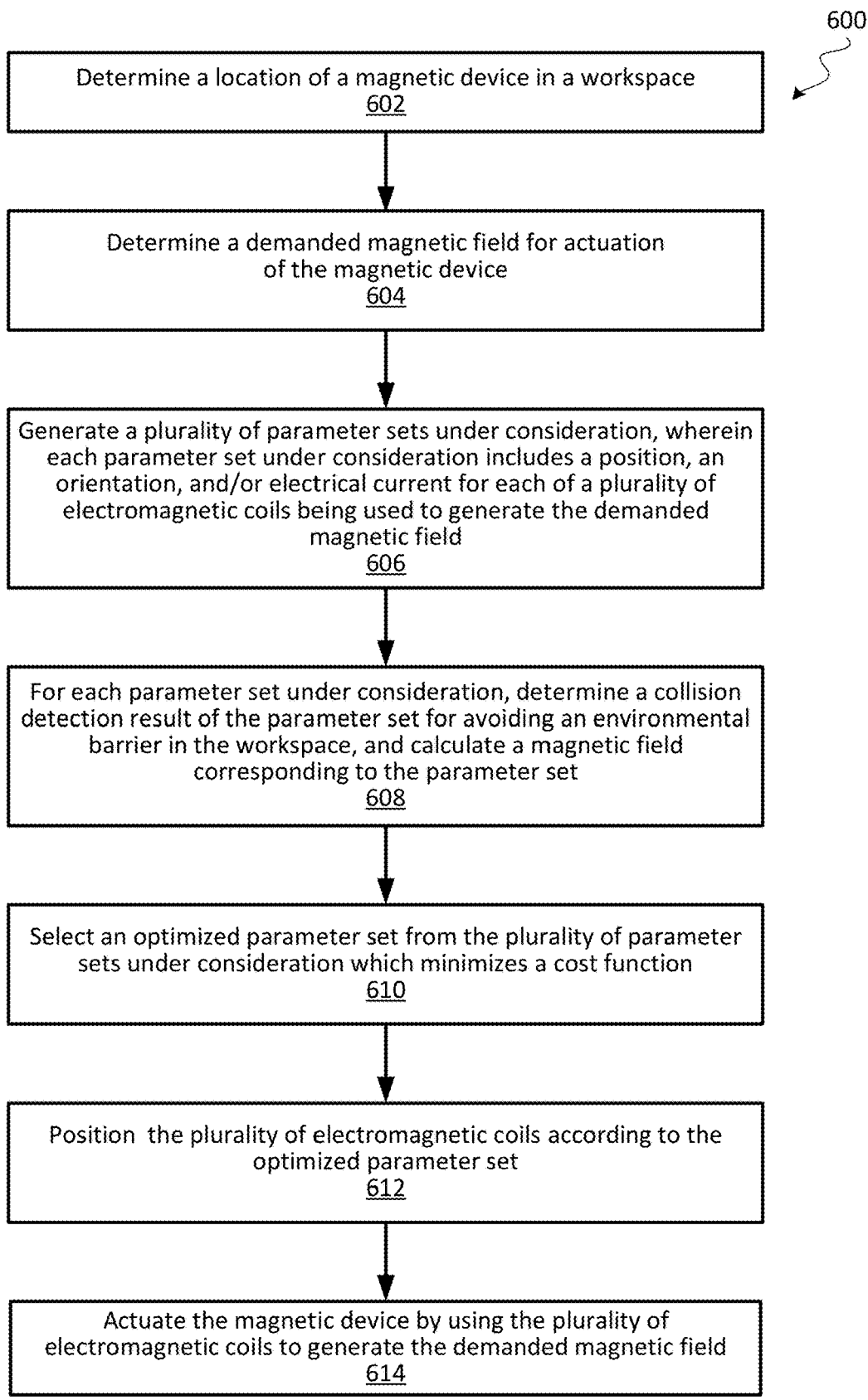
FIG. 6 illustrates a flow chart of a process for magnetic actuation, according to some embodiments.

FIG. 6 illustrates a flow diagram of a process 600 for magnetic actuation of a device, according to some embodiments. Process 600 can be used, for example, by a magnetic actuation system having more than one mobile electromagnetic coils that can move individually or together within a working space, to generate magnetic fields in order to control the demanded tasks of magnetic devices in a body, including but not limited to locomotion, navigation, changing shape, targeted delivery, sensing, tissue manipulation, etc. Examples of magnetically controlled devices may include magnetic robots such as one or more capsule endoscopes, magnetic endoscopes, magnetic laparoscope, catheters, guidewires, microrobots, nanorobots, microrobotic swarms, or other devices, particles or drugs that responds to magnetic field, etc. The technique can also be used to actuate devices in an animal or other volume of substance such as liquid, solid, gas, or a combination thereof.

Process 600 may begin at block 602 by determining a location of the magnetic device being actuated in a workspace. The location of the magnetic device can be determined, for example, by a localization device. At block 604, the demanded magnetic field for actuation of the magnetic device can be determined. The demanded magnetic field can be dependent on the type of magnetic device being actuated and/or the task being performed by the magnetic device. For example, the demanded magnetic field may correspond to the magnetic field necessary to direct movement of the magnetic device in a certain direction. As another example, the demanded magnetic field may correspond to the magnetic field necessary to activate a microrobot, or to release drugs from a magnetically controlled capsule.

At block 606, process 600 may generate multiple parameter sets for consideration. Each parameter set under consideration may include a position and an orientation for each of the electromagnetic coils being used to generate the demanded magnetic field. In some implementations, the parameter set may also include the electrical currents to drive each electromagnetic coil. The multiple parameter sets can be generated in a pseudo-random manner. For example, if process 600 is being initialized, the initial parameter sets can be chosen randomly between a lower bound and an upper bound. The lower and upper bounds may represent the limits on the physical reach of the robotic arm assemblies. In some implementations, the lower and upper bounds can further be reduced based on the previously optimized location of the magnetic device relative to the robotic arm assemblies of the system. If process 600 has already been initialized and a previously optimized parameter set already exists, the multiple parameter sets can be randomly chosen to be within a threshold difference from the previously optimized parameter set.

At block 608, for each parameter set under consideration, a collision detection result of the parameter set for avoiding an environmental barrier in the workspace is determined, and a magnetic field corresponding to the parameter set is calculated. The collision detection can be performed by modelling an environmental barrier as described above, and determining whether the coil positions and orientations in the parameter set would cause interference with the barrier. The barrier can be, for example, the body of a patient and/or other devices or obstructions within the workspace. The magnetic field can be calculated by linear superposition of the individual magnetic field generated by each coil at the corresponding position, orientation, and applied current of the parameter set under consideration.

At block 610, an optimized parameter set that minimizes a cost function is selected from the multiple parameter sets under consideration. The optimized parameter set can be selected through an iterative search process. The cost function can be represented as linear, polynomial, fractional, exponential, and/or logarithmic combination of different weighted components, which can be used to avoid collision with obstructions, generate the demanded magnetic field correctly, reduce electrical currents in each coil to generate the magnetic field, and/or reduce mechanical movements of the mechanical actuation subsystem for improved control bandwidth. Depending on the particular application, the cost function can prioritize or emphasize certain aspects of the cost function such as prioritizing collision avoidance. For example, the cost function may include a first weighted component based on a demanded electrical current for the demanded magnetic field, a second weighted component based on a difference between the parameter set under consideration and a previous optimized parameter set, and a third weighted component based on collision avoidance. In some implementations, if simpler computations are desirable, the cost function may include a first weighted component based on a difference between the demanded magnetic field and the magnetic field corresponding to the parameter set under consideration, a second weighted component based a difference between a demanded magnetic force and the magnetic force corresponding to the parameter set under consideration, and a third weighted component based on collision avoidance. The weighted values can be adjusted based on the application, and the third weight value is typically set at infinity to prevent collision with environmental barriers.

Blocks 606, 608, and 610 collectively can be considered as part of an optimization process. Once the optimized parameter set that minimizes the cost function is selected, the electromagnetic coils of the system can be positioned at block 612 according to the optimized parameter set. Consequently, the magnetic device being controlled can be actuated by using the electromagnetic coils to generate the demanded magnetic field at their optimized positions/orientations and applied electrical currents. The optimization process can be repeated periodically when generating a time-varying magnetic field and gradient, and/or be repeated when the magnetic device being controlled has navigated to a different location within the workspace. For example, when an updated location of the magnetic device is determined by a localization device, the optimization process can be repeated for the updated location of the magnetic device.

Figure 7:
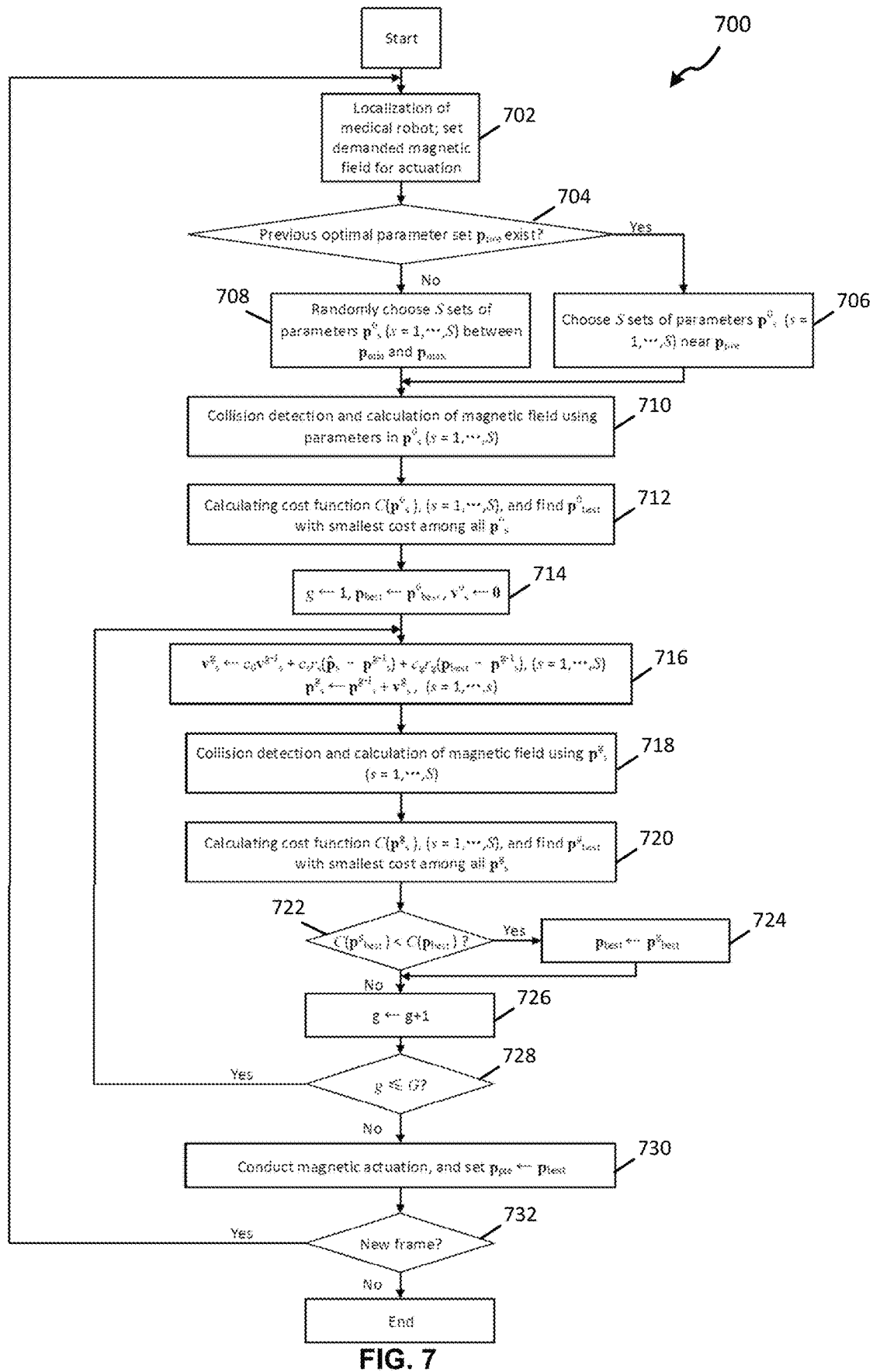
FIG. 7 illustrates a flow chart of an optimization technique, according to some embodiments.

FIG. 7 illustrates a flow chart of a process 700 with additional details of the optimization technique, according to some embodiments. In the calculation process, the parameters to be optimized is depicted as a parameter set p. The optimization will be iterated for G generations, and in each generation, there will be S sets of parameters. The parameter set $p_s^g$ means the $s_{th}$ set in the $g_{th}$ generation (s=1, . . . , S, g=1, . . . , G). $p_{min}$ and $p_{max}$ are the lower and upper boundaries of the parameters, respectively.

The cost function of the optimization process can be defined in the following method. Considering a specific task, if the system has redundant degrees of freedom (DOFs) and the demanded currents can be easily calculated through the inverse model that is introduced above, the parameter set can be defined as $p_g^s = \{õ_{c,1}, \ldots, õ_{c,n}, \tilde{r}_{c,1}, \ldots, \tilde{r}_{c,n}\}$ or a set of parameters that can determine the spatial positions and orientations of the n coils, where n is the number of coils, and the cost function can be defined as:

$$C(p_s^g) = w_1 \sum_{i=1}^{n} \sum_{k=1}^{m} \left(I_i\left(\frac{k}{mf}\right)\right)^2 + w_2 \|p_s^g - p_{pre}\| + w_3 Q(p_s^g) \quad (32)$$

In the equation, $$I_i\left(\frac{k}{mf}\right)$$

is the demanded current for required magnetic field at time $$t = \frac{k}{mf},$$

where f is the frequency of the periodic dynamic field and f=0 for static field. $\|p_s^g - p_{pre}\|$ is the change between the current parameter set and the optimal parameter set at the last state. $Q(p_s^g)$ shows the result of collision detection if parameter set $p_s^g$ is applied. The three elements in the equation are in charge of the demanded currents, mechanical movements and avoid collision, respectively, and $w_1$ to $w_3$ are the weights of each aspect. Usually $w_3 \to \infty$ and $w_1$ and $w_2$ can be assigned based on applications. When $w_1$ is larger, lower current will be applied to achieve higher efficiency; when $w_2$ is larger, mechanical movement during the operation will be reduced due to the less parameter change, and control frequency of the system can be increased. On the other hand, if the system does not have redundant DOFs to complete complicated tasks or inverse calculation of currents is too complex to complete, such as 5-DOF actuation of untethered magnetic robots, the parameter set can be defined as $p_s^g = \{\tilde{o}_{c,1}, \ldots, \tilde{o}_{c,n}, \tilde{r}_{c,1}, \ldots, \tilde{r}_{c,n}, I_1, \ldots, I_n\}$ or a set of parameters that can determine the spatial positions, orientations and currents of the n coils, and the cost function can be defined as $$\mathcal{C}(p_s^g) = w_1\|B - \tilde{B}(p_s^g)\| + w_2\|F - \tilde{F}(p_s^g)\| + w_3 Q(p_s^g) \quad (33)$$

In this cost function, the purpose is to reduce the error of generated magnetic field and force if parameter set $p_g^s$ is applied. B and F are demanded magnetic field strength and force respectively, and $\tilde{B}(p_s^g)$ and $\tilde{F}(p_s^g)$ are the magnetic field and force that is produced under parameter set $p_s^g$, which can be easily calculated through the model that is introduced above. $w_1$ to $w_3$ are the respective weight of those elements. Usually $w_3 \to \infty$ to avoid collision with environmental boundaries.

The optimization on the position and orientation of the mobile electromagnetic coils can be conducted in real-time, during the operation of the system. The inputs of the optimization algorithm include the position of the magnetic medical robot d, form and parameters of magnetic field that is demanded for actuation, etc. The outputs include the optimal position $\hat{o}_{c,i}$ and orientation $\hat{r}_{c,i}$ of the mobile electromagnetic coils, and the currents in the coils $I_i$ (if needed). Every time the input changes, the optimization will be executed once, and the result of optimization, i.e. optimal parameter set, will be saved as $p_{pre}$ to be used in the next optimization. The optimization process can be divided into initialization and searching, as in FIG. 7. If $p_{pre}$ exists, which means that the coils are currently at the state defined by $p_{pre}$, the initial parameter sets of the present optimization will starts from $p_{pre}$, as shown in the following equation:

$$\begin{cases} p_s^0 = p_{pre} & (s = 1) \\ p_s^0 = p_{pre} + \omega rand(p_{min} - p_{pre}, p_{max} - p_{pre}) & (s = 2, \ldots, S) \end{cases} \quad (34)$$

where function rand(a, b) is to generate a random vector between lower boundary a and upper boundary b, and ω is a manually assigned constant between 0 and 1. However, if $p_{pre}$ doesn't exist, the initial parameter sets can be determined as following.

$$p_s^0 = rand(p_{min}, p_{max}) (s = 1, \ldots, S) \quad (35)$$

After the S sets of parameters in the initial generation have been determined, the magnetic field and collision detection function using the S sets of parameters will be calculated, followed by the calculation of cost functions. The parameter set with the best cost will be save as the initial value of global optimum $p_{best}$. Based on the initial parameter sets, the next step is to search for the optimum through G generations of iteration. The S sets of parameters in the $g_{th}$ generation g=(1, ..., G) can be determined by the following equations:

$$\begin{cases} v_s^g = c_0 v_s^{g-1} + c_s r_s(\hat{p}_s - p_s^{g-1}) + c_g r_g(p_{best} - p_s^{g-1}) & (s = 1, \ldots, S) \\ p_s^g = p_s^{g-1} + v_s^g & (s = 1, \ldots, S) \end{cases} \quad (36)$$

In the equations, $v_s^g$ is the speed of the value change of the $s_{th}$ parameter set at the $g_{th}$ generation. It consists of three elements: inertia, influence of its own best till $g_{th}$ generation $\hat{p}_s$, and influence of global best till $g_{th}$ generation $p_{best}$. $c_0$ is inertia weight, $c_s$ and $c_g$ are coefficients that define the personal best's influence and global best's influence, respectively. The coefficients can be determined manually or by specific algorithms. $r_s$ and $r_g$ are random numbers between 0 and 1. After G generations, the global best $p_{best}$ will be sent to the magnetic field generation system and mechanical actuation system for execution, and $p_{pre}$ will be updated as current $p_{best}$t, for the use of next optimization.

Referring to the optimization process shown in FIG. 7, at block 702, localization of the medical robot being controlled can be determined and the demanded magnetic field for actuation can be set. At block 704, a determination is made as to whether a previous optimal parameter set $p_{pre}$ exist. If a previous optimal parameter set does not exist, the system can be initialized by randomly choosing S sets of parameters $p_s^0$ (s=1, ..., S) between $P_{min}$ and $P_{max}$ at block 708. If a previous optimal parameter set exists, the S sets of parameters $p_s^0$ (s=1, ..., S) can be chosen at block 706 to be near the previous optimal parameter set $p_{pre}$. At block 710, collision detection and calculation of magnetic field can be performed using the parameters in $p_s^0$ (s=1, ..., S). At block 712, the cost function $\mathcal{C}(p_s^0)$, (s=1, ..., S), is calculated to find $p_{best}^0$ with smallest cost among all $p^0$, At block 714, the optimized parameter set is selected, and the iterative parameter generation is updated with g←1, $p_{best} \leftarrow p_{best}^0$, $v_s^0 \leftarrow 0$.

At block 716, the next iteration of parameter set generation is performed in accordance with equation (36) above. At block 718, collision detection and calculation of magnetic field can be performed using the parameters in $p_s^g$ (s=1, ..., S). At block 720, the cost function $\mathcal{C}(p_s^g)$, (s=1, ..., S), is calculated to find $p_{best}^g$ with smallest cost among all $p^g$, At block 722, a determination is made as to whether if the parameter set $p_{best}^g$ has a lower cost that the current $p_{best}$: $\mathcal{C}(p_{best}^g) < \mathcal{C}(p_{best})$. If so, then at block 724, the current parameter set is updated as $p_{best} \leftarrow p_{best}^g$. Otherwise, the current parameter set is not updated. At block 724, the iterative generation count is incremented as g←g+1, and at block 728, a determination is made as to whether the iterative generation count is less the target G number of generations. If so, process 700 returns to block 716 to generate additional parameter sets. If the target G number of generations have been reached, then at block 730, magnetic actuation is conducted and the optimized parameter set is updated as $p_{pre} \leftarrow p_{best}$. At block 732, a determination is made as to whether a new frame has occurred. The new frame may correspond to a new interval to update the optimized parameter set, a new localization of the medical device being controlled, etc. If a new frame has occurred, the process can be restarted from block 702.

Figure 8A:
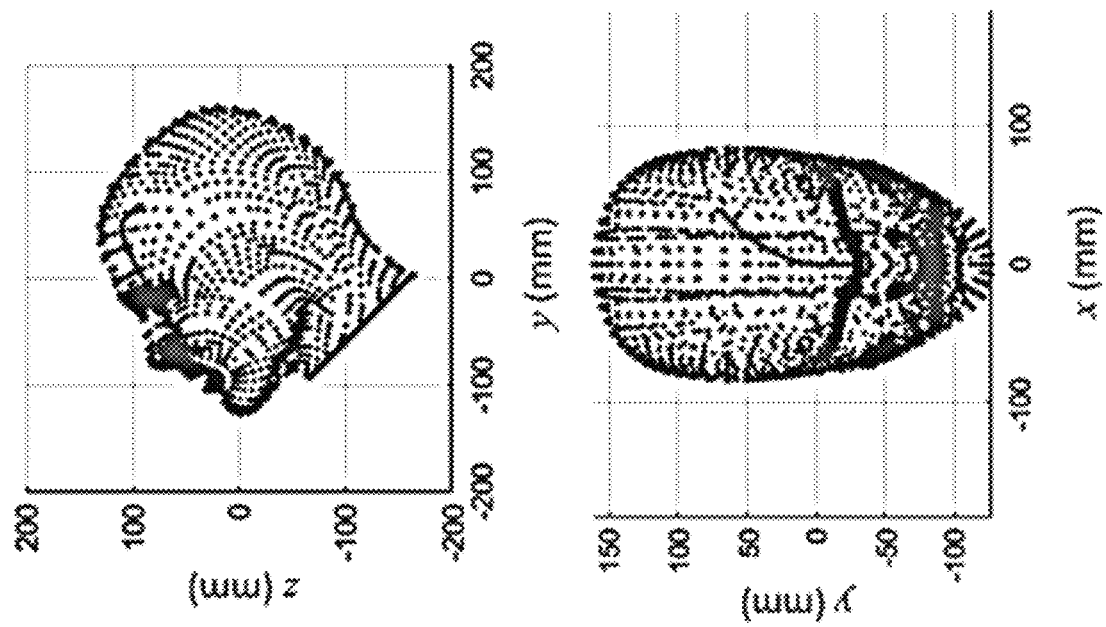
FIG. 8A illustrates simulation results of the trajectory of a magnetic device being actuated, according to some embodiments.
Figure 8A:
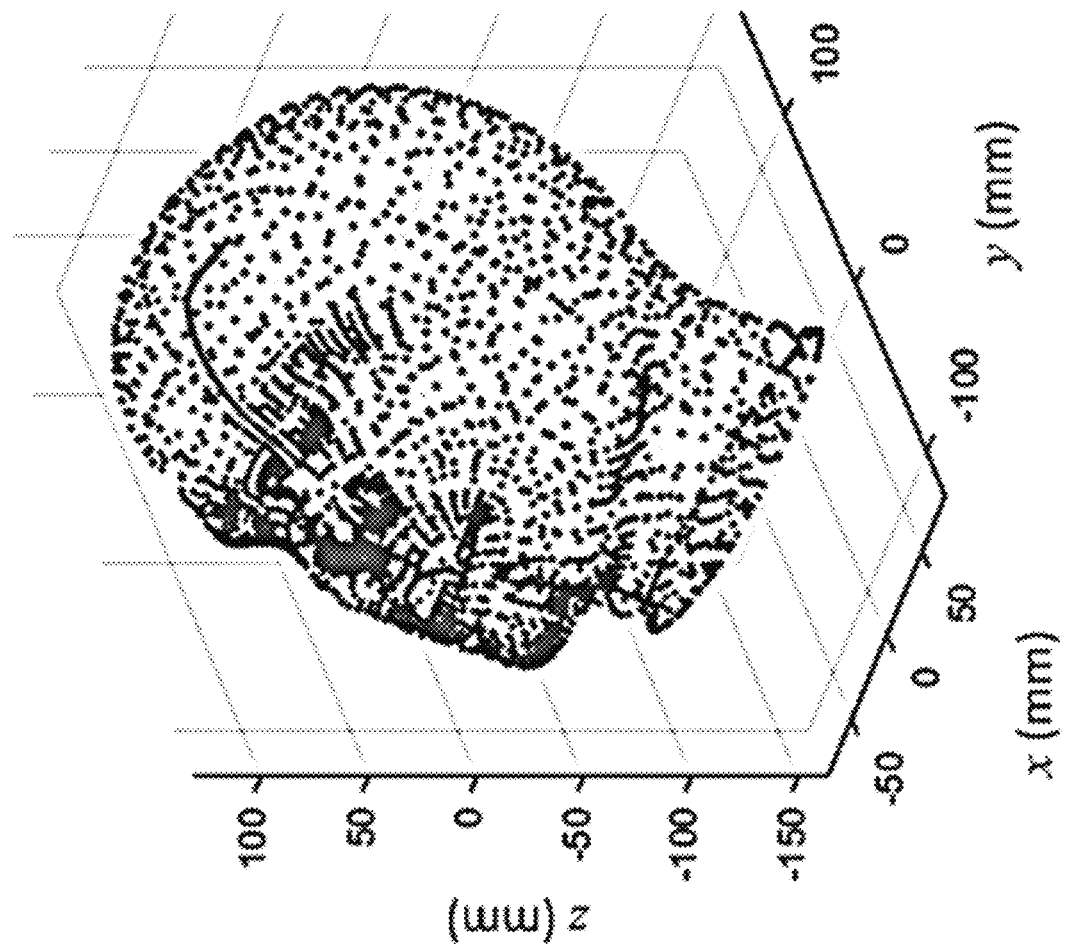
Figures 8B, 8C:
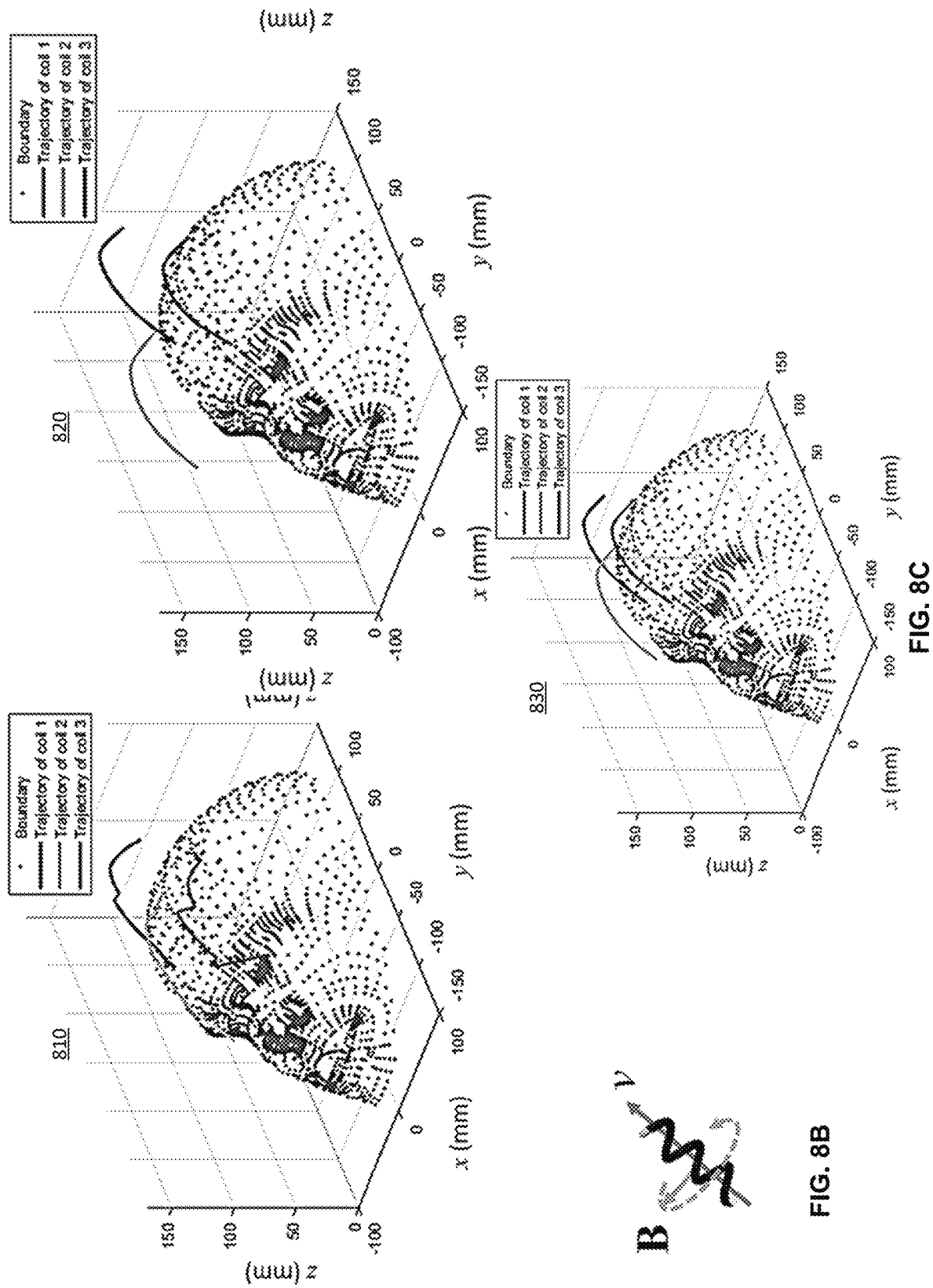
FIG. 8B illustrates a helical robot, according to some embodiments.
FIG. 8C illustrates simulation results of the trajectory of the electromagnetic coils, according to some embodiments.

To demonstrate the capability of the proposed optimization and modeling technique, a simulation was conducted. FIG. 8A illustrates a scenario under which the simulation is conducted. The system is to actuate a helical swimmer to go through a 3D channel (solid line in FIG. 8A), and an environmental barrier with a shape of human head is defined (dots in FIG. 8A). The upper right inlet shows the lateral view and the lower right inlet shows the top view. In the simulation, a hypothetical system that possesses three mobile electromagnetic coils that can move individually is used to actuate a helical medical robot along a predefined 3D channel. The helical robot shown in FIG. 8B exploit a rotating field to move. Rotating field B is applied to actuate the robot along the direction of v as shown in FIG. 8B. The rotating plane is orthogonal to trajectory. The locomotion direction is perpendicular to the rotating plane of the magnetic field and along the axial direction of the robot; the locomotion speed is proportional to the frequency to magnetic field. Assuming the robot is moving inside a channel and the pose of the robot does not need feedback control, the rotating plane of the applied magnetic field is always perpendicular to the channel.

The channel, marked in solid line, is assumed to be part of the vessel inside brain. In this simulation, the mobile coils are actuated tracking the location of the helical robot, so that the robot is always on the axial of the coil. Three different control strategies have been applied for simulation. For the first strategy, the method with real-time optimization described herein is applied. As for the second strategy, the tilting angle of the three coils are manually defined as 45° with the horizontal plane and higher than the location of medical robot, and accordingly, the distance between the coil tips and the robot is set to 80 mm to avoid collision with the barrier. For the third strategy, similar to the second one, the angle is set to 60° and distance is 60 mm to avoid collision.

Figure 8D:
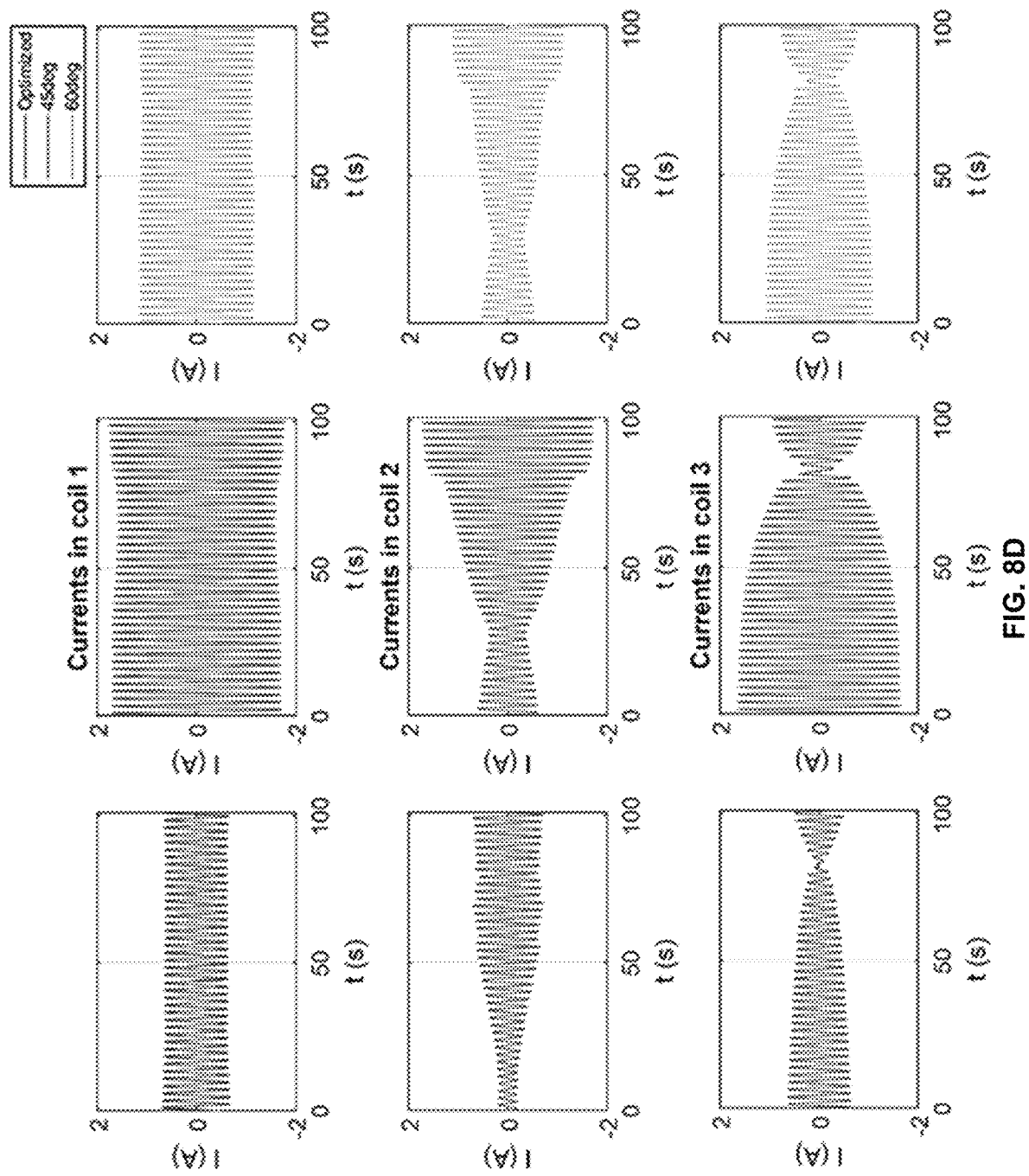
FIG. 8D illustrates the applied electrical currents to the electromagnetic coils, according to some embodiments.

FIG. 8C shows the simulated trajectory of the tip of the mobile electromagnetic coils throughout the actuation process under different control strategies. The coil tip's trajectory using first strategy is labeled 810, using the second strategy is labeled 820, and the trajectory of the third strategy is labeled 830. Three different lines indicate the trajectories of the three coils. The demanded current to complete the task using the three control strategies are shown in FIG. 8D. The upper, middle and lower inlets show the currents in the three respective mobile electromagnetic coils. Electrical currents under the control strategy with optimizations is plotted on the left, electrical currents of second strategy is plotted in the middle, and electrical currents of the third strategy is plotted on the right. According to the simulation, through the entire actuation process, the total demanded current using the strategy with optimization on coil positions is 63.9% and 46.8% less than the other two methods respectively. From the result, the optimization process is able to reduce the electrical current to a great extent and the real-time optimization technique described herein is effective.

Figure 9:
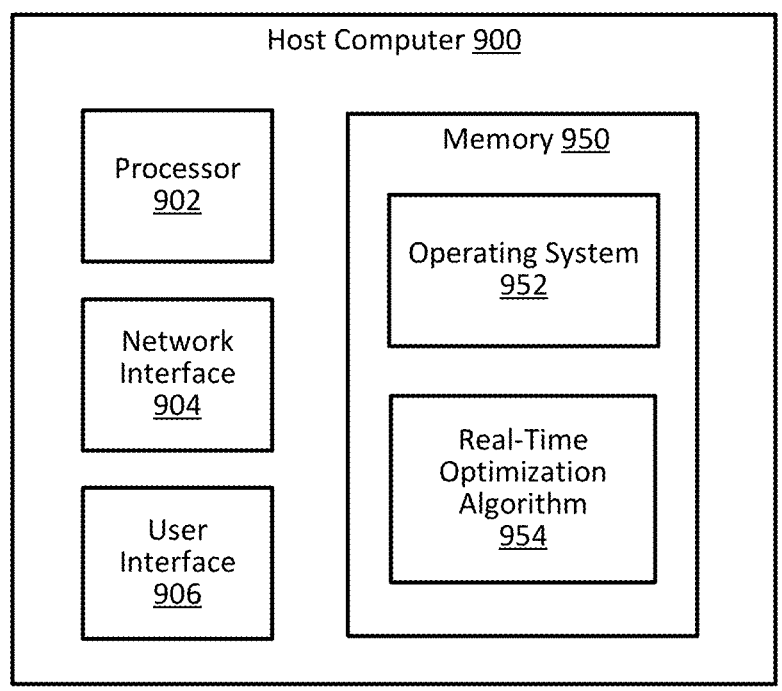
FIG. 9 illustrates a block diagram of a host computer, according to some embodiments.

FIG. 9 illustrates a host computer system 900 that can be used to implement the various aspects of the technique described herein. Host computer system 900 may include a processor 902, a network interface 904, a user interface 906, and a non-transitory computer readable memory 950 storing code executable by processor 902. The host computer system 900 can be a standalone computing device or can be integrated with or communicatively coupled to a medical device such as CT scanner, medical imaging machinery, etc.

Processor 902 can be implemented as one or more integrated circuits (e.g., one or more single core or multicore microprocessors and/or microcontrollers) and is used to control the operation of host computer system 900. Processor 902 can execute a variety of programs in response to program code or computer-readable code stored in memory 950 and can maintain multiple concurrently executing programs or processes. The processor 902 may include an arithmetic logic unit (ALU) to perform computational intensive calculations. The host computer system 900 may include a dedicated ALU separate from processor 902.

Network interface 904 may include one or more transceivers, connectors, or I/O ports that can be used by host computer system 900 to communicate with other devices, to connect with external networks, and/or to transfer data using electronic or physical medium. User interface 906 can include any combination of input and output elements (e.g., pointer device, speaker, display, etc.) to allow a user to interact with and invoke the functionalities of host computer system 900. The user interface 906 may include an integrated display (e.g., flat panel display, touch screen, etc.) or can be coupled to an external display.

Computer readable memory 950 can be implemented using any combination of volatile memories (e.g., DRAM, SRAM), non-volatile memories (e.g., flash memory), and/or any other non-transitory storage medium, or a combination thereof media. Memory 950 may store an operating system 952 and a variety of programs and/or algorithms. For example, memory 950 may store a real-time optimization algorithm 954 such as those described herein. The real-time optimization algorithm 954 can be integrated as part of one or more software applications.

The techniques described herein may involve implementing one or more functions, processes, operations or method steps. The functions, processes, operations or method steps may be implemented as a result of the execution of a set of instructions or software code by a suitably-programmed computing device, microprocessor, data processor, or the like. The set of instructions or software code may be stored in a memory or other form of data storage element which is accessed by the computing device, microprocessor, etc. The set of instructions or software code may be stored on a computer readable medium, such as a random access memory (RAM), a read only memory (ROM), flash memory, a magnetic medium such as a hard-drive or a floppy disk, a steady state drive, or an optical medium such as a CD-ROM. Any such computer readable medium may reside on or within a single computational apparatus and may be present on or within different computational apparatuses within a system or network. The functions, processes, operations or method steps may be implemented by firmware or a dedicated processor, integrated circuit, processing unit (e.g., ALU), etc.

The methods and processes described herein are exemplary in nature, and the methods and processes in accordance with some embodiments may perform one or more of the steps in a different order than those described herein, include one or more additional steps not specially described, omit one or more steps, combine one or more steps into a single step, split up one or more steps into multiple steps, and/or any combination thereof. One or more features from any embodiment may be combined with one or more features of any other embodiment without departing from the scope of the invention.

A recitation of "a," "an," or "the" is intended to mean "one or more" unless specifically indicated to the contrary.

What is claimed is:

1. A magnetic actuation system to generate a magnetic field to actuate a magnetic device disposed inside a volume of substance, comprising:
   a magnetic field generation subsystem having a plurality of mobile electromagnetic coils including at least a first mobile electromagnetic coil and a second electromagnetic coil;
   a mechanical actuation subsystem having a plurality of robotic arm assemblies, including at least a first robotic arm assembly and a second robotic arm assembly, the first robotic arm assembly being connected to the first mobile electromagnetic coil and the second robotic arm assembly being connected to the second mobile electromagnetic coil, the first robotic arm assembly and a second robotic arm assembly being independently movable to position the first and second electromagnetic coils independently of each other; and
   a host computer configured to:
      receive parameters of a desired magnetic field that is demanded for actuation of the plurality of magnetic coils to control the magnetic device;
      determine positions and orientations of each of the plurality of electromagnetic coils to achieve the desired magnetic field;
      determine independent amounts of current for each of the plurality of electromagnetic coils to achieve the desired magnetic field;
      provide independent control signals to each of the plurality of robotic arm assemblies to achieve the positions and orientations of the electromagnetic coils; and
      provide independent control signals to each of the plurality of electromagnetic coils to achieve the independent amounts of current for each of the plurality of electromagnetic coils to achieve the desired magnetic field.

2. The magnetic actuation system of claim 1, wherein the host computer is further configured to
   determine a plurality of sets of possible positions and orientations of the plurality of electromagnetic coils to achieve the desired magnetic field;
   select one of the plurality of sets of the possible positions to provide an optimized set of positions and orientations of the electromagnetic coils that achieves at least one of avoiding a collision with other equipment, minimizing a demanded current, and reducing mechanical movement; and
   provide independent control signals to each of the plurality of robotic arm assemblies to achieve the optimized set of positions and orientations of the electromagnetic coils.

3. The magnetic actuation system of claim 1, wherein the host computer is further configured to select from among a plurality of possible positions of the electromagnetic coils to determine optimized positions and orientations of the plurality of electromagnetic coils; and
   wherein determining the optimized positions and orientations includes minimizing a cost function of a parameter set that includes a position and an orientation of each electromagnetic coil relative to a location of the magnetic device being actuated.

4. The magnetic actuation system of claim 3, wherein minimizing the cost function performs one or more all of the following:
   avoiding collision with obstructions;
   reducing electrical currents in each coil to generate the magnetic field; and
   reducing mechanical movements of the mechanical actuation subsystem for improved control bandwidth.

5. The magnetic actuation system of claim 3, wherein cost function includes a combination of weighted components selected from:
   a weighted component based on a demanded electrical current for the magnetic field;
   a weighted component based on a difference between the parameter set under consideration and a previous optimized parameter set;
   a weighted component based on collision avoidance with other medical equipment;
   a weighted component based on a difference between a target magnetic field and a magnetic field corresponding to the parameter set under consideration; and
   a weighted component based a difference between a target magnetic force and a magnetic force corresponding to the parameter set under consideration.

6. The magnetic actuation system of claim 3, wherein the one or more robotic arm assemblies includes a robotic arm assembly having a plurality of rotatable joints attached to respective robotic arm segments.

7. The magnetic actuation system of claim 4, wherein the robotic arm assembly includes at least four rotatable joints.

8. The magnetic actuation system of claim 7, wherein the at least four rotatable joints include one rotatable joint that rotates on a horizontal plane and three rotatable joints that rotate on a vertical plane.

9. The magnetic actuation system of claim 1, wherein the magnetic field generation subsystem includes a microcontroller to control a set of amplifiers and/or power supplies to apply electrical currents to the electromagnetic coils.

10. The magnetic actuation system of claim 1, wherein the mechanical actuation subsystem includes a microcontroller to control a set of motors controlling the one or more robotic arm assemblies to place the electromagnetic coils in the positions and orientations.

11. The magnetic actuation system of claim 1, wherein the mechanical actuation subsystem includes a medical imaging device at an end of a robotic arm segment.

12. The magnetic actuation system of claim 1, wherein mechanical actuation subsystem includes a track and a slider.

13. The magnetic actuation system of claim 1, further comprising a localization device to track a location of the magnetic device being actuated.

14. The magnetic actuation system of claim 1, wherein the generated magnetic field is a linear superposition of individual magnetic fields generated by each electromagnetic coil.

15. The magnetic actuation system of claim 1 wherein the positions and orientations of the plurality of electromagnetic coils to achieve the desired magnetic field are determined using a world frame of reference; and
   the host computer is further configured to:
      convert the world frame of reference of the positions and orientations of the plurality of electromagnetic coils into a robotic arm frame of reference;

provide independent control signals to each of the plurality of robotic arm assemblies based on the robotic arm frame of reference to achieve the positions and orientations of the electromagnetic coils.

16. A magnetic actuation system to generate a magnetic field to actuate a magnetic device disposed inside a volume of substance, comprising:

a magnetic field generation subsystem having a plurality of mobile electromagnetic coils including at least a first mobile electromagnetic coil and a second electromagnetic coil;

a mechanical actuation subsystem having a plurality of robotic arm assemblies, including at least a first robotic arm assembly and a second robotic arm assembly, the first robotic arm assembly being connected to the first mobile electromagnetic coil and the second robotic arm assembly being connected to the second mobile electromagnetic coil, the first robotic arm assembly and a second robotic arm assembly being independently movable to position the first and second electromagnetic coils independently of each other; and one or more processors;

non-transitory, computer-readable media having instructions for causing the one or more processors to:

receive parameters of a desired magnetic field that is demanded for actuation of the plurality of magnetic coils to control the magnetic device;

determine positions and orientations of the plurality of electromagnetic coils to achieve the desired magnetic field;

provide independent control signals to each of the plurality of robotic arm assemblies to achieve the positions and orientations of the electromagnetic coils;

determine a plurality of sets of possible positions and orientations of the plurality of electromagnetic coils to achieve the desired magnetic field;

select one of the plurality of sets of the possible positions to provide an optimized set of positions and orientations of the electromagnetic coils that achieves at least one of avoiding a collision with other medical devices and imaging devices, minimizing a demanded current, and reducing mechanical movement;

provide independent control signals to each of the plurality of robotic arm assemblies to achieve the optimized set of positions and orientations of the electromagnetic coils;

convert a world frame of reference of the positions and orientations of the plurality of electromagnetic coils into a robotic arm frame of reference; and provide independent control signals to each of the plurality of robotic arm assemblies based on the robotic arm frame of reference to achieve the positions and orientations of the electromagnetic coils.

* * * * *